(12) United States Patent  
Ackermann et al.

(10) Patent No.: US 6,995,263 B2  
(45) Date of Patent: Feb. 7, 2006

(54) INDOLYL AND DIHYDROINDOLYL DERIVATIVES, THEIR MANUFACTURE AND USE AS PHARMACEUTICAL AGENTS

(75) Inventors: Jean Ackermann, Riehen (CH); Johannes Aebi, Basel (CH); Alfred Binggeli, Basel (CH); Uwe Grether, Loerrach (DE); Georges Hirth, Colmar (FR); Bernd Kuhn, Liestal (CH); Hans-Peter Maerki, Basel (CH); Markus Meyer, Neuenburg (DE); Peter Mohr, Basel (CH); Matthew Blake Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 10/978,144

(22) Filed: Oct. 29, 2004

(65) Prior Publication Data  
US 2005/0096353 A1 May 5, 2005

(30) Foreign Application Priority Data  
Nov. 5, 2003 (EP) ................................. 03104083

(51) Int. Cl.  
*C07D 401/04* (2006.01)  
*C07D 401/14* (2006.01)  
*C07D 403/02* (2006.01)

(52) U.S. Cl. .................................. 544/333; 546/277.4  
(58) Field of Classification Search ............. 546/277.4; 544/333  
See application file for complete search history.

(56) References Cited

U.S. PATENT DOCUMENTS

2004/0209936 A1  10/2004  Bratton et al.

FOREIGN PATENT DOCUMENTS

| GB | 2163150 A | * | 2/1986 |
|---|---|---|---|
| WO | WO 02/08188 A1 | | 1/2002 |
| WO | WO 03/018553 A1 | | 3/2003 |
| WO | WO 03/027069 | | 4/2003 |
| WO | WO 03/027076 | | 4/2003 |
| WO | WO 03/040107 | | 5/2003 |
| WO | WO 03/074051 A1 | | 9/2003 |
| WO | WO 03/084916 | | 10/2003 |
| WO | WO 2004/063190 A1 | | 7/2004 |
| WO | WO 2004/073606 A2 | | 9/2004 |

OTHER PUBLICATIONS

Nugent, et al., "Potentiation of Glucose Uptake in 3T3-L1 Adipocytes by PPARγ Agonists Is Maintained in Cells Expressing a PPARγ . . . " Molecular Endocrinology 15(10): 1729-1738 (2001).*  
Anal. Biochem. 257: 112-119.  
Belostotskii, Anatoly M., et. al., Tetrahedron Lett (1994), 35(28), 5075-6.  
E.J. Corey, et. al., Am. Chem. Soc (1987) 109, 5551-5553.  
Guerre-Millo, et. al., J. Biol Chem (2000) 275: 16638-16642.  
Lobiner, et. al., Tetrahedron Lett. (1984), 25, 2535-3536.  
S.W. McCombie, et. al., Bioorganic & Medicinal Chemistry Ltrs 13 (2003) 567-571.  
Oliver, et. al., Proc Nat Acad Sci USA (2001) 98: 5306-11.  
P.V. Ramachandran, e.t al., Tetrahedron: Asymmetry (1994) 5, 1061-1074.  
TETRAHEDRON Letters 43 (42), 7617-7619 (2002).

* cited by examiner

*Primary Examiner*—Joseph K. McKane  
*Assistant Examiner*—Andrew B. Freistein  
(74) *Attorney, Agent, or Firm*—George W. Johnston; Patricia S. Rocha-Tramaloni

(57) ABSTRACT

This invention relates to compounds of the formula

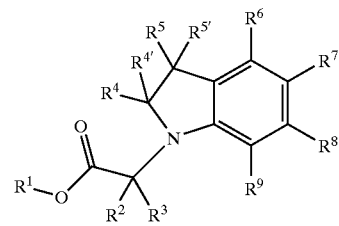

I wherein one of $R^6$, $R^7$ and $R^8$ is

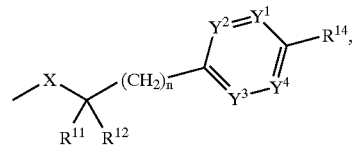

and X, $Y^1$ to $Y^4$, $R^1$ to $R^{14}$ and n are as defined in the description, and to all enantiomers and pharmaceutically acceptable salts and/or esters thereof. The invention further relates to pharmaceutical compositions containing such compounds, to a process for their preparation and to their use for the treatment and/or prevention of diseases which are modulated by PPARδ and/or PPARα agonists.

25 Claims, No Drawings

INDOLYL AND DIHYDROINDOLYL DERIVATIVES, THEIR MANUFACTURE AND USE AS PHARMACEUTICAL AGENTS

SUMMARY OF THE INVENTION

The present invention is concerned with novel indolyl or dihydroindolyl derivatives of the formula

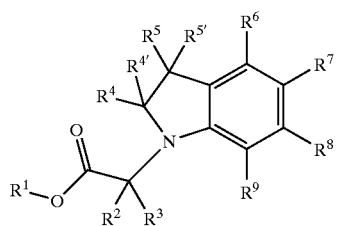

wherein
$R^{1-9}$ are as described herein.

It has been found that compounds of formula I are useful as lipid modulators and insulin sensitizers. In particular, compounds of formula I are PPAR activators.

BACKGROUND OF THE INVENTION

Peroxisome Proliferator Activated Receptors (PPARs) are members of the nuclear hormone receptor superfamily. The PPARs are ligand-activated transcription factors that regulate gene expression and control multiple metabolic pathways. Three subtypes have been described which are PPARα, PPARδ (also known as PPARβ), and PPARγ. PPARδ is ubiquitously expressed. PPARα is predominantly expressed in the liver, kidney and heart. There are at least two major isoforms of PPARγ. PPARγ1 is expressed in most tissues, and the longer isoform, PPARγ2 is almost exclusively expressed in adipose tissue. The PPARs modulate a variety of physiological responses including regulation of glucose- and lipid-homeostasis and metabolism, energy balance, cell differentiation, inflammation and cardiovascular events.

Approximately half of all patients with coronary artery disease have low concentrations of plasma HDL cholesterol. The atheroprotective function of HDL was first highlighted almost 25 years ago and stimulated exploration of the genetic and environmental factors that influence HDL levels. The protective function of HDL comes from its role in a process termed reverse cholesterol transport. HDL mediates the removal of cholesterol from cells in peripheral tissues including those in the atherosclerotic lesions of the arterial wall. HDL then delivers its cholesterol to the liver and sterol-metabolizing organs for conversion to bile and elimination. Data from the Framingham study showed that HDL-C levels are predictive of coronary artery disease risk independently of LDL-C levels. The estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial side-effects limit the therapeutic potential of this approach.

As many as 90% of the 14 million diagnosed type 2 diabetic patients in the US are overweight or obese, and a high proportion of type 2 diabetic patients have abnormal concentrations of lipoproteins. The prevalence of total cholesterol >240 mg/dl is 37% in diabetic men and 44% in women. The respective rates for LDL-C >160 mg/dl are 31% and 44%, respectively, and for HDL-C <35 mg/dl 28% and 11%, respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and afflicts 80–90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in later stage of disease, due to exhaustion and failure of pancreatic insulin-producing capacity. Thus T2D is a cardiovascular-metabolic syndrome associated with multiple comorbidities including insulin resistance, dyslipidemia, hypertension, endothelial dysfunction and inflammatory atherosclerosis.

First line treatment for dyslipidemia and diabetes generally involves a low-fat and low-glucose diet, exercise and weight loss. However, compliance can be moderate, and as the disease progresses, treatment of the various metabolic deficiencies becomes necessary with e.g. lipid-modulating agents such as statins and fibrates for dyslipidemia and hypoglycemic drugs, e.g. sulfonylureas or metformin for insulin resistance. A promising new class of drugs has recently been introduced that resensitizes patients to their own insulin (insulin sensitizers), thereby restoring blood glucose and triglyceride levels to normal, and in many cases, obviating or reducing the requirement for exogenous insulin. Pioglitazone (Actos™) and rosiglitazone (Avandia™) belong to the thiazolidinedione (TZD) class of PPARγ-agonists and were the first in their class to be approved for NIDDM in several countries. These compounds, however, suffer from side effects, including rare but severe liver toxicity (as seen with troglitazone). They also increase body weight in patients. Therefore, new, more efficacious drugs with greater safety and lower side effects are urgently needed. Recent studies provide evidence that agonism of PPARδ would result in compounds with enhanced therapeutic potential, i. e. such compounds should improve the lipid profile, with a superior effect on HDL-C raising compared to current treatments and with additional positive effects on normalization of insulin-levels (Oliver et al; Proc Nat Acad Sci USA 2001; 98: 5306–11). Recent observations also suggest that there is an independent PPARα mediated effect on insulin-sensitization in addition to its well known role in reducing triglycerides (Guerre-Millo et al; J Biol Chem 2000; 275: 16638–16642). Thus selective PPARδ agonists or PPARδ agonists with additional PPARα activity may show superior therapeutic efficacy without the side-effects such as the weight gain seen with PPARγ agonists.

The novel compounds of the present invention exceed the compounds known in the art, inasmuch as they bind to and selectively activate PPARδ or coactivate PPARδ and PPARα simultaneously and very efficiently, and with much improved pharmacokinetic properties. Therefore, these compounds combine the anti-dyslipidemic and anti-glycemic effects of PPARδ and PPARα activation with no effect on PPARγ. Consequently, HDL cholesterol is increased, triglycerides lowered (=improved lipid profile) and plasma glucose and insulin are reduced (=insulin sensitization). In addition, such compounds may also lower LDL cholesterol, decrease blood pressure and counteract inflammatory atherosclerosis. Furthermore, such compounds may also be useful for treating inflammatory diseases such as rheumatoid arthritis, osteoarthritis, and psoriasis. Since multiple facets of combined dyslipidemia and the T2D disease syndrome are addressed by PPARδ-selective agonists and PPARδ and α coagonists, they are expected to have an enhanced therapeutic potential compared to the compounds already known in the art.

The compounds of the present invention further exhibit improved pharmacological properties compared to known compounds.

DETAILED DESCRIPTION OF THE INVENTION

The present invention relates to indolyl or dihydroindolyl derivatives of the formula

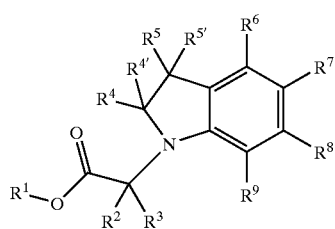

I wherein $R^1$ is hydrogen or $C_{1-7}$-alkyl;

$R^2$ and $R^3$ independently from each other are hydrogen or $C_{1-7}$-alkyl;

$R^4$ and $R^5$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl or fluoro-$C_{1-7}$-alkyl;

$R^{4'}$ and $R^{5'}$ together form a double bond, or $R^{4'}$ and $R^{5'}$ are hydrogen;

$R^6$, $R^7$, $R^8$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^6$, $R^7$ and $R^8$ is

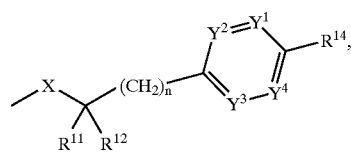

wherein

X is S, O, or $NR^{10}$;

$R^{10}$ is hydrogen, $C_{1-7}$-alkyl, $C_{3-7}$-cycloalkyl, or fluoro-$C_{1-7}$-alkyl;

$R^{11}$ and $R^{12}$ are independently from each other hydrogen, $C_{1-7}$-alkyl, $C_{3-7}$-cycloalkyl, fluoro-$C_{1-7}$-alkyl or fluoro;

$Y^1$, $Y^2$, $Y^3$ and $Y^4$ are N or C—$R^{13}$ and 1 or 2 of $Y^1$, $Y^2$, $Y^3$ and $Y^4$ are N and the other ones are C—$R^{13}$;

$R^{13}$ is selected from the group consisting of hydrogen, $C_{1-7}$-alkyl, $C_{3-7}$-cycloalkyl, $C_{3-7}$-cycloalkyl-$C_{1-7}$-alkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;

$R^{14}$ is aryl or heteroaryl;

n is 0, 1 or 2; and pharmaceutically acceptable salts and/or esters thereof.

Unless otherwise indicated the following definitions are set forth to illustrate and define the meaning and scope of the various terms used to describe the invention herein.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

The term "lower alkyl" or "$C_{1-7}$-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the groups specifically exemplified herein.

The term "halogen" refers to fluorine, chlorine, bromine and iodine.

The term "fluoro-lower alkyl" or "fluoro-$C_{1-7}$-alkyl" refers to lower alkyl groups which are mono- or multiply substituted with fluorine. Examples of fluoro-lower alkyl groups are e.g. —$CF_3$, —$CH_2CF_3$, —$CH(CF_3)_2$ and the groups specifically exemplified herein.

The term "alkoxy" refers to the group R'—O—, wherein R' is alkyl. The term "lower-alkoxy" or "$C_{1-7}$-alkoxy" refers to the group R'—O—, wherein R' is lower-alkyl. Examples of lower-alkoxy groups are e.g. methoxy, ethoxy, propoxy, isopropoxy, butoxy, isobutoxy and hexyloxy. Preferred are the lower-alkoxy groups specifically exemplified herein.

The term "alkylthio" refers to the group R'—S—, wherein R' is alkyl. The term "lower-alkylthio" or "$C_{1-7}$-alkylthio" refers to the group R'—S—, wherein R' is lower-alkyl. Examples of $C_{1-7}$-alkylthio groups are e.g. methylthio or ethylthio. Preferred are the lower-alkylthio groups specifically exemplified herein.

The term "mono- or di-$C_{1-7}$-alkyl-amino" refers to an amino group, which is mono- or disubstituted with $C_{1-7}$-alkyl. A mono-$C_{1-7}$-alkyl-amino group includes for example methylamino or ethylamino. The term "di-$C_{1-7}$-alkyl-amino" includes for example dimethylamino, diethylamino or ethylmethylamino. Preferred are the mono- or di-$C_{1-7}$-alkylamino groups specifically exemplified herein.

The term "carboxy-lower alkyl" or "carboxy-$C_{1-7}$-alkyl" refers to lower alkyl groups which are mono- or multiply substituted with a carboxy group (—COOH). Examples of carboxy-lower alkyl groups are e.g. —$CH_2$—COOH (carboxymethyl), —$(CH_2)_2$—COOH (carboxyethyl) and the groups specifically exemplified herein.

The term "alkanoyl" refers to the group R'—CO—, wherein R' is alkyl. The term "lower-alkanoyl" or "$C_{1-7}$-alkanoyl" refers to the group R'—O—, wherein R' is lower-alkyl. Examples of lower-alkanoyl groups are e.g. ethanoyl (acetyl) or propionyl. Preferred are the lower-alkoxy groups specifically exemplified herein.

The term "lower alkenyl" or "$C_{2-7}$-alkenyl", alone or in combination, signifies a straight-chain or branched hydrocarbon residue comprising an olefinic bond and up to 7, preferably up to 6, particularly preferred up to 4 carbon atoms. Examples of alkenyl groups are ethenyl, 1-propenyl, 2-propenyl, isopropenyl, 1-butenyl, 2-butenyl, 3-butenyl and isobutenyl. A preferred example is 2-propenyl.

The term "lower alkinyl" or "$C_{2-7}$-alkinyl", alone or in combination, signifies a straight-chain or branched hydrocarbon residue comprising a triple bond and up to 7, preferably up to 6, particularly preferred up to 4 carbon atoms. Examples of alkinyl groups are ethinyl, 1-propinyl, or 2-propinyl.

The term "cycloalkyl" or "$C_{3-7}$-cycloalkyl" denotes a saturated carbocyclic group containing from 3 to 7 carbon atoms, such as cyclopropyl, cyclobutyl, cyclopentyl, cyclohexyl or cycloheptyl.

The term "aryl" relates to the phenyl or naphthyl group, preferably the phenyl group, which can optionally be mono- or multiply-substituted, particularly mono- or di-substituted by halogen, hydroxy, CN, $CF_3$, $NO_2$, $NH_2$, N(H, lower-alkyl), N(lower-alkyl)$_2$, carboxy, aminocarbonyl, lower-alkyl, lower fluoroalkyl, lower-alkoxy, lower fluoroalkoxy, aryl and/or aryloxy. Preferred substituents are halogen, $CF_3$, lower-alkyl and/or lower-alkoxy. Preferred are the specifically exemplified aryl groups.

The term "heteroaryl" refers to an aromatic 5 or 6-membered ring which can comprise 1, 2 or 3 atoms selected from nitrogen, oxygen and/or sulphur such as furyl, pyridyl, 1,2-, 1,3- and 1,4-diazinyl, thienyl, isoxazolyl, oxazolyl, imidazolyl, or pyrrolyl. The term "heteroaryl" further refers to bicyclic aromatic groups comprising two 5- or 6-membered rings, in which one or both rings can contain 1, 2 or 3 atoms selected from nitrogen, oxygen or sulphur such as e.g. indole or quinoline, or partially hydrogenated bicyclic aromatic groups such as e.g. indolinyl. A heteroaryl group may have a substitution pattern as described earlier in connection with the term "aryl". Preferred heteroaryl groups are e.g. thienyl and furyl which can optionally be substituted as described above, preferably with halogen, $CF_3$, lower-alkyl and/or lower-alkoxy.

The term "protecting group" refers to groups such as e.g. acyl, alkoxycarbonyl, aryloxycarbonyl, silyl, or imine-derivatives, which are used to temporarily block the reactivity of functional groups. Well known protecting groups are e.g. t-butyloxycarbonyl, benzyloxycarbonyl, fluorenylmethyloxycarbonyl or diphenylmethylene which can be used for the protection of amino groups, or lower-alkyl-, β-trimethylsilylethyl- and β-trichloroethyl-esters, which can be used for the protection of carboxy groups.

"Isomers" are compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center".

The term "pharmaceutically acceptable salts" embraces salts of the compounds of formula (I) with pharmaceutically acceptable bases such as alkali salts, e.g. Na- and K-salts, alkaline earth salts, e.g. Ca- and Mg-salts, and ammonium or substituted ammonium salts, such as e.g. trimethylammonium salts. The term "pharmaceutically acceptable salts" also relates to such salts.

The compounds of formula (I) can also be solvated, e.g. hydrated. The solvation can be effected in the course of the manufacturing process or can take place e.g. as a consequence of hygroscopic properties of an initially anhydrous compound of formula (I) (hydration). The term pharmaceutically acceptable salts also includes pharmaceutically acceptable solvates.

The term "pharmaceutically acceptable esters" embraces derivatives of the compounds of formula (I), in which a carboxy group has been converted to an ester. Lower-alkyl, hydroxy-lower-alkyl, lower-alkoxy-lower-alkyl, amino-lower-alkyl, mono- or di-lower-alkyl-amino-lower-alkyl, morpholino-lower-alkyl, pyrrolidino-lower-alkyl, piperidino-lower-alkyl, piperazino-lower-alkyl, lower-alkyl-piperazino-lower-alkyl and aralkyl esters are examples of suitable esters. The methyl, ethyl, propyl, butyl and benzyl esters are preferred esters. The methyl and ethyl esters are especially preferred. The term "pharmaceutically acceptable esters" furthermore embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

Preferably, the invention relates to compounds of the formula

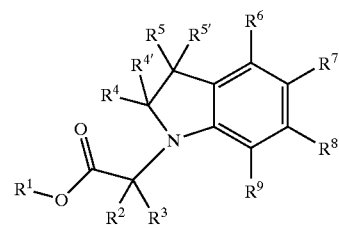

I wherein $R^1$ is hydrogen or $C_{1-7}$-alkyl;

$R^2$ and $R^3$ independently from each other are hydrogen or $C_{1-7}$-alkyl;

$R^4$ and $R^5$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl or fluoro-$C_{1-7}$-alkyl;

$R^{4'}$ and $R^{5'}$ together form a double bond, or $R^{4'}$ and $R^{5'}$ are hydrogen;

$R^6$, $R^7$, $R^8$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;

and one of $R^6$, $R^7$ and $R^8$ is

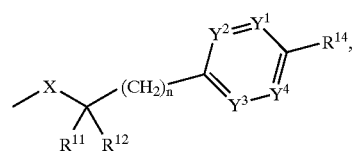

wherein

X is S, O, or $NR^{10}$;

$R^{10}$ is hydrogen, $C_{1-7}$-alkyl, $C_{3-7}$-cycloalkyl, or fluoro-$C_{1-7}$-alkyl;

$R^{11}$ and $R^{12}$ are independently from each other hydrogen, $C_{1-7}$-alkyl, $C_{3-7}$-cycloalkyl, fluoro-$C_{1-7}$-alkyl or fluoro;

$Y^1$, $Y^2$, $Y^3$ and $Y^4$ are N or C—$R^{13}$ and 1 or 2 of $Y^1$, $Y^2$, $Y^3$ and $Y^4$ are N and the other ones are C—$R^{13}$;

$R^{13}$ is selected from the group consisting of hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;

$R^{14}$ is aryl or heteroaryl;

n is 0, 1 or 2; and all enantiomers and pharmaceutically acceptable salts and/or esters thereof.

Preferred compounds of formula I of the present invention are compounds of formula

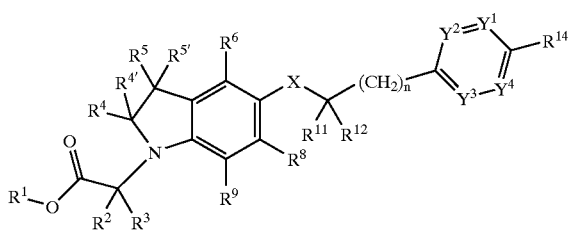

I-A wherein
X, $Y^1$ to $Y^4$, $R^1$, $R^2$, $R^3$, $R^4$, $R^{4'}$, $R^5$, $R^{5'}$, $R^{11}$, $R^{12}$, $R^{14}$ and n are as defined herein before;

$R^6$, $R^8$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and all enantiomers and pharmaceutically acceptable salts and/or esters thereof.

Especially preferred are those compounds of formula I-A, wherein $R^6$, $R^8$ and $R^9$ are hydrogen.

Also preferred are compounds of formula I of the present invention having the formula

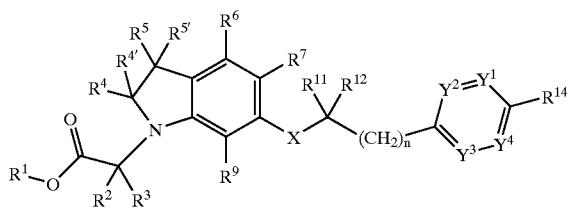

I-B wherein
X, $Y^1$ to $Y^4$, $R^1$, $R^2$, $R^3$, $R^4$, $R^{4'}$, $R^5$, $R^{5'}$, $R^{11}$, $R^{12}$, $R^{14}$ and n are as defined herein before;

$R^6$, $R^7$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and all enantiomers and pharmaceutically acceptable salts and/or esters thereof.

Especially preferred are those compounds of formula I-B, wherein $R^6$, $R^7$ and $R^9$ are hydrogen.

Furthermore, preferred compounds of formula I according to the present invention have the formula

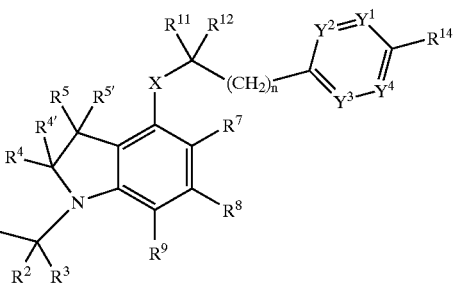

I-C wherein
X, $Y^1$ to $Y^4$, $R^1$, $R^2$, $R^3$, $R^4$, $R^{4'}$, $R^5$, $R^{5'}$, $R^{11}$, $R^{12}$, $R^{14}$ and n are as defined herein before;

$R^7$, $R^8$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and all enantiomers and pharmaceutically acceptable salts and/or esters thereof.

More preferred are those compounds of formula I-C, wherein $R^7$, $R^8$ and $R^9$ are hydrogen.

Especially preferred are compounds of formula I according to the present invention, wherein $R^1$ is hydrogen.

Further preferred compounds of formula I according to the present invention are those, wherein $R^2$ and $R^3$ independently from each other are hydrogen or methyl.

Preferred compounds of formula I according to this invention are also those, wherein $R^{4'}$ and $R^{5'}$ together form a double bond. Such compounds have the formula

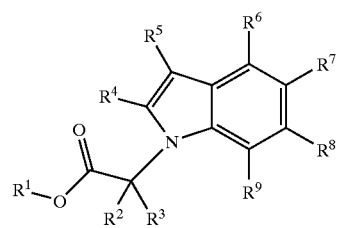

I-D wherein $R^1$ to $R^9$ are as defined herein before.

Also preferred are compounds of formula I according to the present invention, wherein $R^4$ and $R^5$ are hydrogen.

Furthermore, compounds of formula I according to this invention are preferred, wherein X is O.

Also preferred are compounds of formula I according to this invention, wherein X is $NR^{10}$, and $R^{10}$ is hydrogen, $C_{1-7}$-alkyl, $C_{3-7}$-cycloalkyl or fluoro-$C_{1-7}$-alkyl, with those compounds of formula I, wherein $R^{10}$ is $C_{1-7}$-alkyl, being more preferred.

Further preferred compounds of formula I are those, wherein X is S.

Compounds of formula I according to the present invention, wherein $R^{11}$ and $R^{12}$ are hydrogen, are also preferred.

The integer n is 0, 1 or 2. Preferred compounds of formula I are those, wherein n is 0 or 1.

$Y^1$, $Y^2$, $Y^3$ and $Y^4$ signify N or C—$R^{13}$, provided that 1 or 2 of $Y^1$, $Y^2$, $Y^3$ and $Y^4$ are N and the other ones are C—$R^{13}$. $R^{13}$ is selected from the group consisting of hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, and $C_{1-7}$-alkanoyl-$C_{1-7}$-alkyl.

Preferred compounds of the present invention are for example those, wherein 1 of $Y^1$, $Y^2$, $Y^3$ and $Y^4$ is N and the other ones are C—$R^{13}$, thus meaning compounds containing a pyridyl group. Especially preferred are those compounds of formula I, wherein $Y^1$ is N and $Y^2$, $Y^3$ and $Y^4$ are C—$R^{13}$, e. g. compounds of formula I containing the group

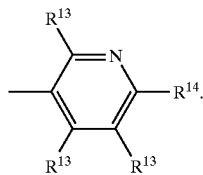

Further preferred compounds of the present invention are those, wherein 2 of $Y^1$, $Y^2$, $Y^3$ and $Y^4$ are N and the other ones are C—$R^{13}$, thus meaning compounds containing a pyrazinyl group or a pyrimidinyl group or a pyridazinyl group.

Especially preferred are compounds of formula I, wherein $Y^1$ and $Y^4$ are N and $Y^2$ and $Y^3$ are C—$R^{13}$, e. g. compounds of formula I containing the pyrimidinyl group

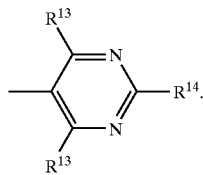

Also preferred are compounds of formula I, wherein $Y^1$ and $Y^3$ are N and $Y^2$ and $Y^4$ are C—$R^{13}$, e. g. compounds of formula I containing the pyrazinyl group

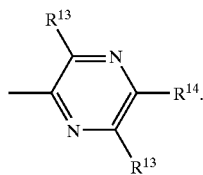

$R^{13}$ is preferably independently selected from hydrogen, $C_{1-7}$-alkyl, fluoro-$C_{1-7}$-alkyl, $C_{3-7}$-cycloalkyl and $C_{1-7}$-alkoxy-$C_{1-7}$-alkyl. Especially preferred are compounds of formula I, wherein at least one $R^{13}$ group is $C_{1-7}$-alkyl, fluoro-$C_{1-7}$-alkyl, $C_{3-7}$-cycloalkyl or $C_{1-7}$-alkoxy-$C_{1-7}$-alkyl.

Especially preferred are compounds of formula I according to the present invention, wherein $Y^1$ is N and $Y^2$, $Y^3$ and $Y^4$ are C—$R^{13}$ or wherein $Y^1$ and $Y^4$ are N and $Y^2$ and $Y^3$ are C—$R^{13}$, with those compounds wherein at least one $R^{13}$ group is $C_{1-7}$-alkyl, $C_{3-7}$-cycloalkyl, fluoro-$C_{1-7}$-alkyl or $C_{1-7}$-alkoxy-$C_{1-7}$-alkyl, being more preferred.

Compounds of formula I of the present invention, wherein $R^{14}$ is aryl, are preferred. More preferred are those compounds of formula I, wherein $R^{14}$ is unsubstituted phenyl or phenyl substituted with one to three groups selected from $C_{1-7}$-alkyl, $C_{1-7}$-alkoxy, halogen, fluoro-$C_{1-7}$-alkyl, fluoro-$C_{1-7}$-alkoxy and cyano, with those compounds, wherein $R^{14}$ is phenyl substituted with halogen, fluoro-$C_{1-7}$-alkoxy, or fluoro-$C_{1-7}$-alkyl, being particularly preferred. Especially preferred are those compounds, wherein $R^{14}$ is 4-trifluoromethylphenyl. Also preferred are those compounds, wherein $R^{14}$ is 4-trifluoromethoxyphenyl.

Particularly preferred compounds of formula I of the present invention are the following:

{5-[4-(2-methoxy-ethyl)-2-(4-trifluoromethyl-phenyl)-pyrimidin-5-ylmethoxy]-indol-1-yl}-acetic acid;

{5-[4-methyl-2-(4-trifluoromethyl-phenyl)-pyrimidin-5-ylmethoxy]-indol-1-yl}-acetic acid;

{5-[4-cyclopropyl-2-(4-trifluoromethyl-phenyl)-pyrimidin-5-ylmethoxy]-indol-1-yl}-acetic acid;

(5-{methyl-[4-methyl-2-(4-trifluoromethyl-phenyl)-pyrimidin-5-ylmethyl]-amino}-indol-1-yl)-acetic acid;

{6-[2-methyl-6-(4-trifluoromethyl-phenyl)-pyridin-3-ylmethoxy]-indol-1-yl}-acetic acid;

{6-[2-methyl-6-(4-trifluoromethyl-phenyl)-pyridin-3-ylmethoxy]-2,3-dihydro-indol-1-yl}-acetic acid;

{6-[4-cyclopropyl-2-(4-trifluoromethyl-phenyl)-pyrimidin-5-ylmethoxy]-indol-1-yl}-acetic acid;

(6-{2-[2-methyl-6-(4-trifluoromethyl-phenyl)-pyridin-3-yl]-ethoxy}-indol-1-yl)-acetic acid;

{6-[6-(4-trifluoromethoxy-phenyl)-pyridin-3-ylmethoxy]-indol-1-yl}-acetic acid;

{6-[2-methyl-6-(3-trifluoromethyl-phenyl)-pyridin-3-ylmethoxy]-indol-1-yl}-acetic acid;

(4-{2-[2-methyl-6-(4-trifluoromethyl-phenyl)-pyridin-3-yl]-ethoxy}-indol-1-yl)-acetic acid;

{6-[4-(2-methoxy-ethyl)-2-(6-trifluoromethyl-pyridin-3-yl)-pyrimidin-5-ylmethoxy]-indol-1-yl}-acetic acid;

{6-[4-trifluoromethyl-6-(4-trifluoromethyl-phenyl)-pyridin-3-ylmethoxy]-indol-1-yl}-acetic acid;

{6-[4-(2-methoxy-ethyl)-6-methyl-2-(4-trifluoromethyl-phenyl)-pyrimidin-5-ylmethoxy]-indol-1-yl}-acetic acid;

{6-[2-methyl-4-trifluoromethyl-6-(4-trifluoromethyl-phenyl)-pyridin-3-ylmethoxy]-indol-1-yl}-acetic acid;

{6-[2-methyl-6-(4-trifluoromethoxy-phenyl)-4-trifluoromethyl-pyridin-3-ylmethoxy]-indol-1-yl}-acetic acid;

{6-[6-(4-trifluoromethoxy-phenyl)-4-trifluoromethyl-pyridin-3-ylmethoxy]-indol-1-yl}-acetic acid;

{6-[2-cyclopropylmethyl-6-(4-trifluoromethoxy-phenyl)-4-trifluoromethyl-pyridin-3-ylmethoxy]-indol-1-yl}-acetic acid;

(6-{2-[4-cyclopropyl-2-(4-trifluoromethyl-phenyl)-pyrimidin-5-yl]-ethoxy}-indol-1-yl)-acetic acid;

{6-[6-(4-trifluoromethoxy-phenyl)-2-trifluoromethyl-pyridin-3-ylmethoxy]-indol-1-yl}-acetic acid; and {6-[2-cyclopropyl-6-(4-trifluoromethoxy-phenyl)-4-trifluoromethyl-pyridin-3-ylmethoxy]-indol-1-yl}-acetic acid.

Especially preferred compounds of the present invention include the following:

{5-[4-(2-methoxy-ethyl)-2-(4-trifluoromethyl-phenyl)-pyrimidin-5-ylmethoxy]-indol-1-yl}-acetic acid;

(5-{methyl-[4-methyl-2-(4-trifluoromethyl-phenyl)-pyrimidin-5-ylmethyl]-amino}-indol-1-yl)-acetic acid;

{6-[2-methyl-6-(4-trifluoromethyl-phenyl)-pyridin-3-yl-methoxy]-indol-1-yl}-acetic acid;
{6-[4-(2-methoxy-ethyl)-2-(6-trifluoromethyl-pyridin-3-yl)-pyrimidin-5-ylmethoxy]-indol-1-yl}-acetic acid;
{6-[2-methyl-4-trifluoromethyl-6-(4-trifluoromethyl-phenyl)-pyridin-3-ylmethoxy)-indol-1-yl}-acetic acid;
{6-[6-(4-trifluoromethoxy-phenyl)-4-trifluoromethyl-pyridin-3-ylmethoxy]-indol-1-yl}-acetic acid;
(6-{2-[4-cyclopropyl-2-(4-trifluoromethyl-phenyl)-pyrimidin-5-yl]-ethoxy}-indol-1-yl)-acetic acid;
{6-[6-(4-trifluoromethoxy-phenyl)-2-trifluoromethyl-pyridin-3-ylmethoxy]-indol-1-yl}-acetic acid; and
{6-[2-cyclopropyl-6-(4-trifluoromethoxy-phenyl)-4-trifluoromethyl-pyridin-3-ylmethoxy]-indol-1-yl}-acetic acid.

Furthermore, the pharmaceutically acceptable salts of the compounds of formula I and the pharmaceutically acceptable esters of the compounds of formula I individually constitute preferred embodiments of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

It will be appreciated, that the compounds of general formula I in this invention may be derivatised at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises reacting a compound of formula

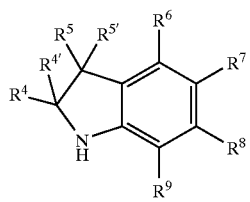

II wherein $R^4$ to $R^9$ are as defined as herein before, with a compound of formula

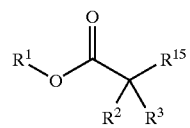

III wherein $R^1$ is $C_{1-7}$-alkyl, $R^2$ and $R^3$ are as defined herein before and $R^{15}$ is halogen, triflate or another leaving group, to obtain a compound of formula

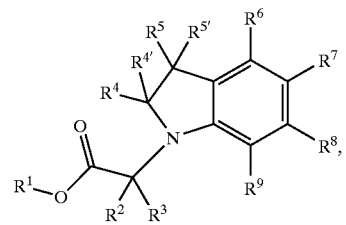

I wherein $R^1$ is $C_{1-7}$-alkyl and $R^2$ to $R^9$ are as defined herein before, and optionally hydrolysing the ester group to obtain a compound of formula I, wherein $R^1$ is hydrogen.

or, alternatively, reacting a compound of formula

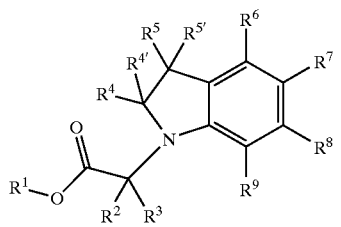

IV wherein $R^1$ is $C_{1-7}$-alkyl, $R^2$ to $R^5$ are as defined hereinbefore and $R^6$, $R^7$, $R^8$ and $R^9$ are independently selected from hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl, and cyano, and one of $R^6$, $R^7$ or $R^8$ is —OH, —SH or —NHR$^{10}$ with $R^{10}$ being hydrogen, $C_{1-7}$-alkyl, $C_{3-7}$-cycloalkyl or fluoro-$C_{1-7}$-alkyl, with a compound of formula

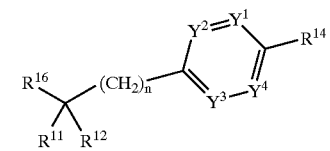

V wherein
$Y^1$, $Y^2$, $Y^3$, $Y^4$, $R^{11}$, $R^{12}$, $R^{14}$ and n are as defined herein before and $R^{16}$ is —OH, —Cl, —Br, —I or another leaving group, to obtain a compound of formula

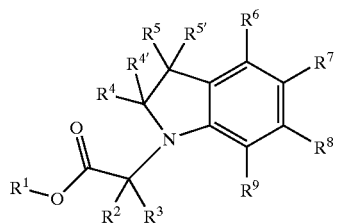

I wherein $R^1$ is $C_{1-7}$-alkyl and $R^2$ to $R^9$ are as defined herein before, and optionally hydrolysing the ester group to obtain a compound of formula I, wherein $R^1$ is hydrogen.

As described above, the compounds of formula I of the present invention can be used as medicaments for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases (such as e.g. Crohn's disease, inflammatory bowel disease, colitis, pancreatitis, cholestasis/fibrosis of the liver, rheumatoid arthritis, osteoarthritis, psoriasis and other skin disorders, and diseases that have an inflammatory component such as e.g. Alzheimer's disease or impaired/improvable cognitive function) and proliferative diseases (cancers such as e.g. liposarcoma, colon cancer, prostate cancer, pancreatic cancer and breast cancer). The use as medicament for the treatment of low HDL cholesterol levels, high LDL cholesterol levels, high triglyceride levels, and the metabolic syndrome (syndrome X) is preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are modulated by PPARδ and/or PPARα agonists. Examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In another embodiment, the invention relates to a method for the treatment and/or prevention of diseases which are modulated by PPARδ and/or PPARα agonists, which method comprises administering a compound of formula (I) to a human or animal. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

The invention further relates to the use of compounds as defined above for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases.

In addition, the invention relates to the use of compounds as defined above for the preparation of medicaments for the treatment and/or prevention of diseases which are modulated by PPARδ and/or PPARα agonists. Preferred examples of such diseases are diabetes, particularly non-insulin dependent diabetes mellitus, increased lipid and cholesterol levels, particularly low HDL-cholesterol, high LDL-cholesterol, or high triglyceride levels, atherosclerotic diseases, metabolic syndrome (syndrome X), obesity, elevated blood pressure, endothelial dysfunction, procoagulant state, dyslipidemia, polycystic ovary syndrome, inflammatory diseases such as rheumatoid arthritis, osteoarthritis, psoriasis and other skin disorder, and proliferative diseases. Such medicaments comprise a compound as defined above.

The compounds of formula (I) can be manufactured by the methods given below, by the methods given in the examples or by analogous methods. Appropriate reaction conditions for the individual reaction steps are known to a person skilled in the art. Starting materials are either commercially available or can be prepared by methods analogous to the methods given below, by methods described in references cited in the text or in the examples, or by methods known in the art.

Scheme 1
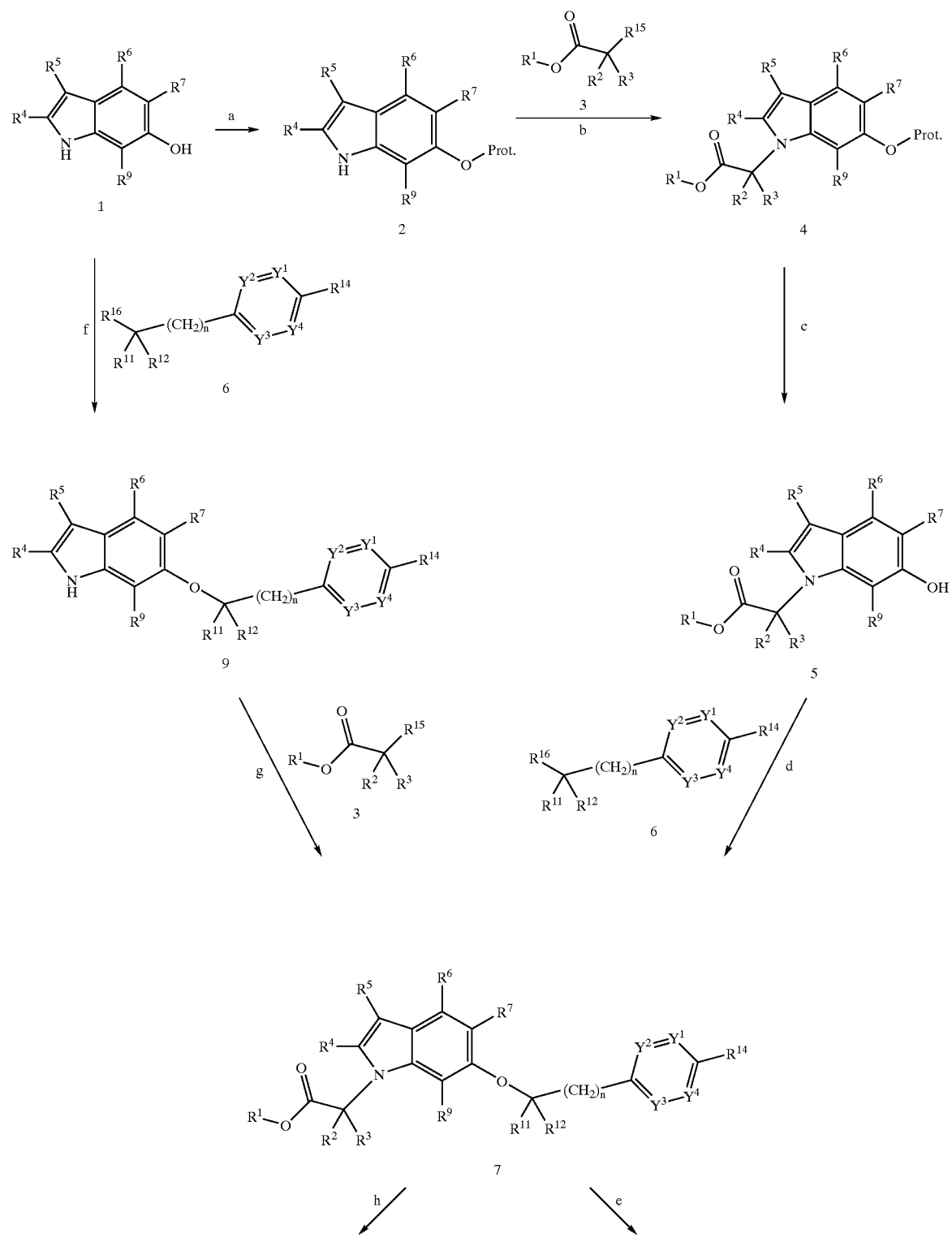

-continued

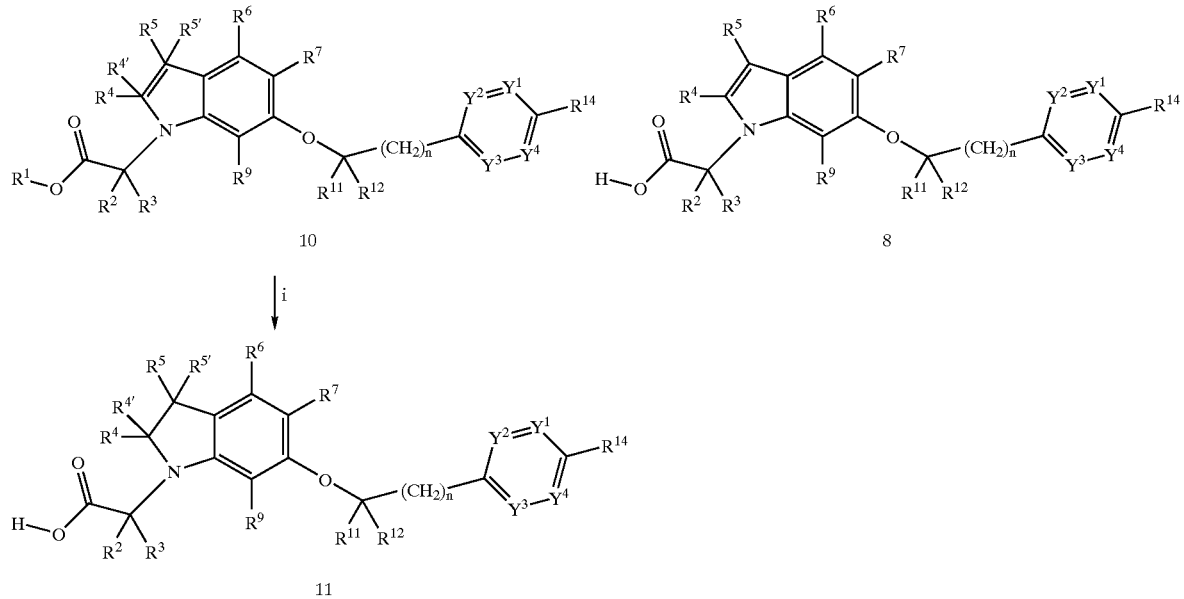

Compounds of formula I with X being equal to oxygen (compounds 7, 8, 10 and 11 in scheme 1) can be synthesized according to the methods depicted in scheme 1 for $R^8$ being equal to

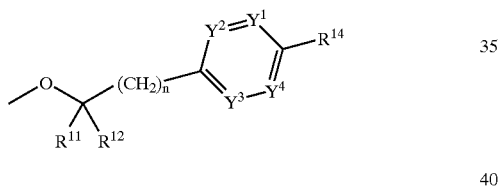

with $Y^1$ to $Y^4$, $R^{11}$, $R^{12}$, $R^{14}$ and n having the meanings as defined herein before.

The same reaction sequences can be applied to synthesize compounds of formula I where $R^6$ or $R^7$ is equal to

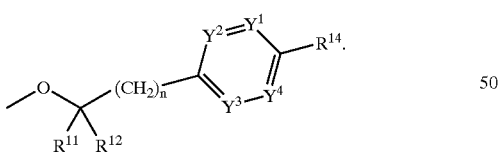

6-Hydroxyindoles 1 and the regioisomeric 4- and 5-hydroxyindoles are commercially available, known or can be synthesized by methods known in the art. The hydroxy function of compounds 1 can be protected by methods described in the literature, e. g. by treating them with tert-butyldimethylsilyl chloride in the presence of imidazole, preferably at room temperature in solvents like N,N-dimethylformamide, to obtain the corresponding tert-butyldimethylsilyl ethers 2 (step a). N-Alkylation of intermediates 2 with carboxylic acid ester 3, where $R^{15}$ can be equal to e. g. chlorine, bromine, triflate or another leaving group, delivers indoles 4 and can be performed by standard technology; e. g. in the presence of $K_2CO_3$ or $Cs_2CO_3$ at temperatures between 10° C. and the reflux temperature of the solvent in a solvent like acetonitrile or acetone or in the presence of sodium hydride at temperatures between −10° C. and 50° C. in a solvent like N,N-dimethylformamide (step b). Ester derivatives 3 are commercially available or can be synthesized by methods known in the art. Deprotection of indoles 4 by methods described in the literature, e. g. by treatment with tetrabutyl ammonium fluoride at temperatures between −15° C. and ambient temperature in a solvent like tetrahydrofuran, provided that the protection group is a silyl ether, gives hydroxyindoles 5 (step c). Heterocyclic compounds 6 (prepared as outlined in schemes 5–8) are condensed with hydroxyindoles 5 according to well known procedures: if $R^{16}$ represents a hydroxy group e. g. via Mitsunobu-reaction, with triphenylphosphine and di-tert-butyl-, diisopropyl- or diethyl-azodicarboxylate as reagents, or by using tributylphosphine and N,N,N',N'-tetramethyl azodicarboxamide; this transformation is preferably carried out in a solvent like toluene, dichloromethane or tetrahydrofuran at ambient temperature. Alternatively, if $R^{16}$ represents a halide, mesylate or tosylate moiety, heterocyclic compounds 6 can be reacted with hydroxyindoles 5 in solvents like N,N-dimethylformamide, acetonitrile, acetone or methyl-ethyl ketone in the presence of a weak base like cesium or potassium carbonate at a temperature ranging from room temperature to 140° C., preferably around 50° C., to yield ether compounds 7 (step d). Those can optionally be hydrolyzed according to standard procedures, e. g. by treatment with an alkali hydroxide like LiOH or NaOH in a polar solvent mixture like tetrahydrofuran/ethanol/water leading to carboxylic acids 8 (step e).

2,3-Dihydroindole compounds 10 can be synthesized via partial reduction of indoles 7, e. g. by treating them with sodium cyano borohydride, preferably at ambient temperature in solvents like acetic acid or solvent mixtures like acetic acid/dichloro-methane (step h). Dihydroindole esters 10 can optionally be hydrolyzed under the conditions given in step e to yield carboxylic acids 11 (step i). If heterocyclic compounds 6 (prepared as described in schemes 5–8) and/or the hydroxyindoles 5 contain chiral centers, ester compounds 7 and 10 and carboxylic acids 8 and 11 are obtained as mixtures of diastereomers or enantiomers, which can be separated by methods well known in the art, e. g. (chiral) HPLC chromatography or crystallization. Racemic compounds can e. g. be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent.

Carboxylic acid esters 7 can alternatively be synthesized via regioselective condensation of heterocyclic compounds 6 with hydroxyindoles 1 under the conditions given in step d (step f) and subsequent alkylation of the obtained ethers 9 with alkylating reagents 3 as described for the synthesis of esters 4 in step b (step g).

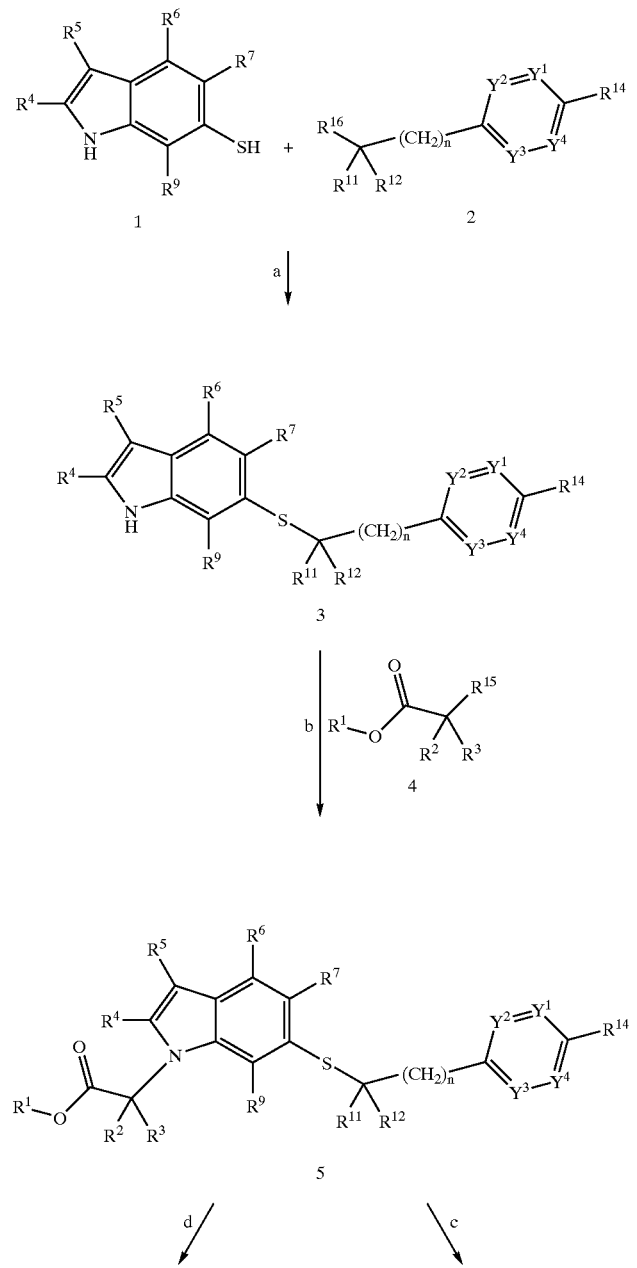

Scheme 2

-continued

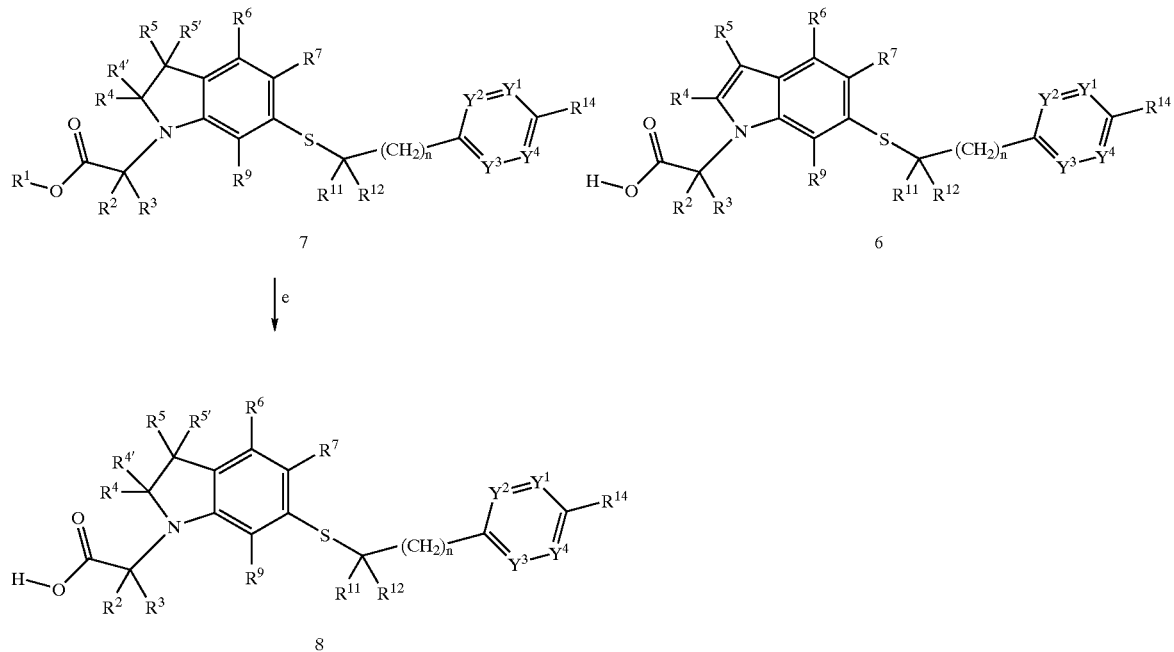

Compounds of formula (I) with X being equal to sulfur (compounds 5, 6, 7 and 8 in scheme 2) can be synthesized according to the methods depicted in scheme 2 for $R^8$ being equal to

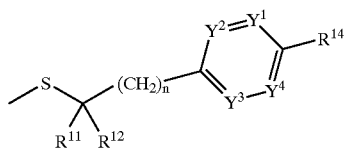

with $Y^1$ to $Y^4$, $R^{11}$, $R^{12}$, $R^{14}$ and n having the meanings as defined herein before.

The same reaction sequences can be applied to synthesize compounds of formula (I) where $R^6$ or $R^7$ is equal to

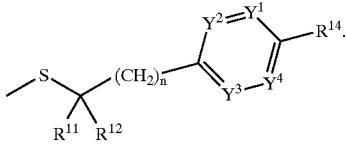

6-Mercaptoindoles 1 and the regioisomeric 4- and 5-mercaptoindoles are known, can be synthesized by methods known in the art (compare e. g. M. Matsumoto, N. Watanabe, *Heterocycles* 1987, 26, 913–916) or are prepared from the analogous N-protected hydroxyindoles via replacement of the hydroxy group by a thiol function by methods known in the art, like e. g. in analogy to a three step sequence described in J. Labelled Compounds & Radiopharmaceuticals 43(7), 683–691, 2000: i) transformation of the aromatic hydroxy group into its trifluoromethanesulfonate (triflic anhydride, triethylamine, dichloromethane, at low temperature, preferably around −30° C.); ii) treatment of the triflate with triisopropylsilanethiolate, tetrakis(triphenylphosphine)-palladium(0) in solvent mixtures like toluene and tetrahydrofuran in a temperature range between 60° C. and 150° C.; iii) treatment of the silyl sulfide with hydrogen chloride in methanol preferably around 0° C. to liberate the aromatic SH moiety.

Alkylation of mercaptoindoles 1 with heterocyclic compounds 2 (step a) can be performed in analogy to the reaction of hydroxyindoles 1 with heterocyclic compounds 6 (scheme 1, step f). Subsequent reaction of thioethers 3 with electrophiles 4 (step b) and transformation of the resulting esters 5 to carboxylic acids 6 (step c) or 2,3-dihydroindole derivatives 7 and 8 (steps d and e) can be accomplished as described for the synthesis of the analogous compounds with X being equal to oxygen (scheme 1, steps g, e, h and i). If heterocyclic compounds 2 (prepared as described in schemes 5–8) and/or electrophiles 4 and/or mercaptoindoles 1 contain chiral centers, ester compounds 5 and 7 and carboxylic acids 6 and 8 are obtained as mixtures of diastereomers or enantiomers, which can be separated by methods well known in the art, e. g. (chiral) HPLC chromatography or crystallization. Racemic compounds can e. g. be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent.

Scheme 3
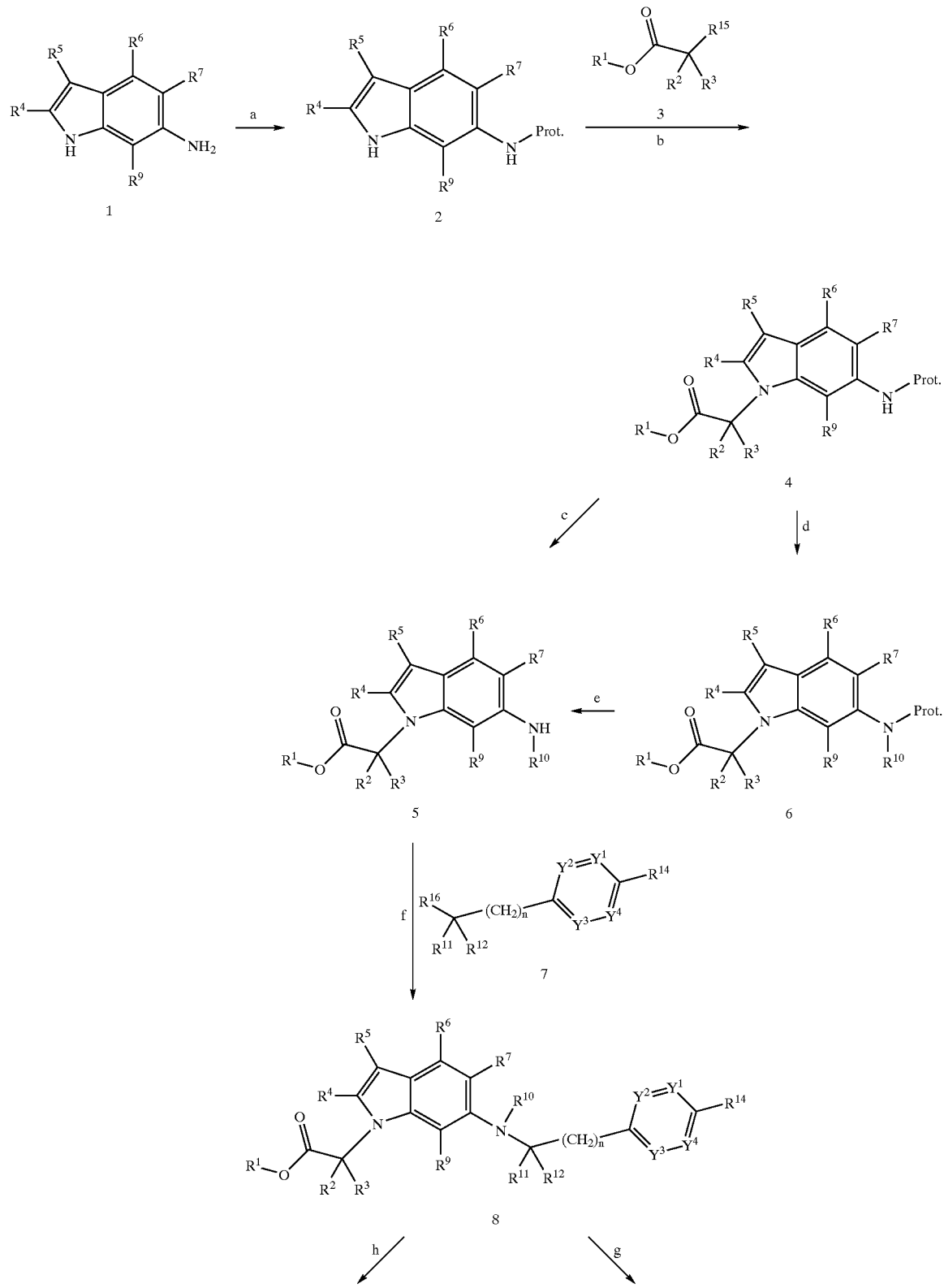

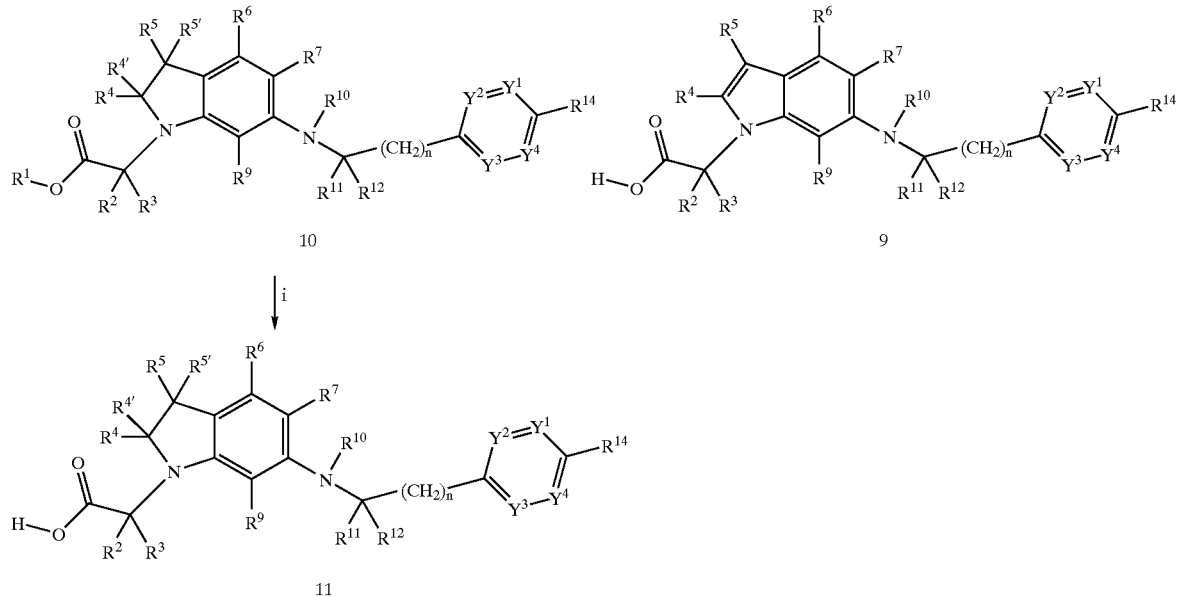

Compounds of formula I with X being equal to $NR^{10}$ (compounds 8, 9, 10 and 11 in scheme 3) can be synthesized according to the methods depicted in scheme 3 for $R^8$ being equal to

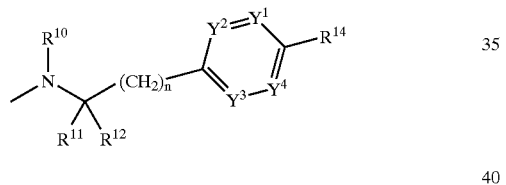

with $Y^1$ to $Y^4$, $R^{10}$, $R^{11}$, $R^{12}$, $R^{14}$ and n having the meanings as defined herein before.

The same reaction sequences can be applied to synthesize compounds of formula (I) where $R^6$ or $R^7$ is equal to

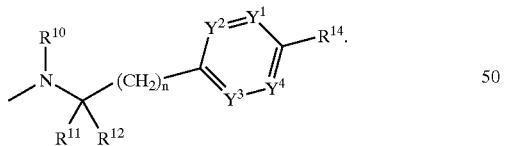

6-Aminoindoles 1 and the regioisomeric 4- and 5-aminoindoles are commercially available, known or can be synthesized by methods known in the art, e. g. starting from the analogous hydroxyindoles. In such intermediates, optionally carrying one or more protective functions, the aromatic hydroxy group can be replaced by an amino function, e. g. by applying the following three step sequence described in Tetrahedron Letters 43(42), 7617–7619(2002): i) transformation of the hydroxyindole moiety into its trifluoro-methanesulfonate (triflic anhydride, 2,6-lutidine, 4-dimethylaminopyridine, dichloromethane, 0° C. to room temperature; ii) treatment of the triflate with benzophenone imine, di-palladium-tris(dibenzylideneacetone) complex, S-(−)-2,2'-bis(diphenylphosphino)-1,1'-binaphthyl, cesium carbonate, toluene, in a Schlenk tube at temperatures around 120° C.; iii) treatment with catalytic amounts of hydrochloric acid in wet tetrahydrofuran preferably at room temperature to liberate the aromatic $NH_2$ moiety. This amino function of compounds 1 can be protected by methods described in the literature, e. g. by treatment with di-tert-butyl dicarbonate optionally in the presence of a base like e. g. triethylamine, preferably at ambient temperature in solvents like methanol, tetrahydrofuran or dichloromethane, to yield indoles 2 (step a). Alkylation at the nitrogen in position 1 of intermediates 2 with carboxylic acid ester 3, where $R^{15}$ can be equal to e. g. chlorine, bromine, triflate or another leaving group, delivers indoles 4 and can be performed by standard technology; e. g. in the presence of $K_2CO_3$ or $Cs_2CO_3$ at temperatures between 10° C. and the reflux temperature of the solvent in a solvent like acetonitrile, acetone or N,N-dimethylformamide (step b). Removal of the protecting group under standard conditions, e. g. by using trifluoroacetic acid in dichloromethane or hydrochloric acid in dioxane, preferably at temperatures between 0° C. and ambient temperature, affords amines 5 with $R^{10}$ being equal to hydrogen (step c). Intermediates 4 can optionally be alkylated at the nitrogen in 6-position using sodium hydride and a reactive alkyl halogenide/mesylate or triflate to give compounds 6 (step d) which can be deprotected as described in step c to obtain amines 5 with $R^{10} \neq$ hydrogen (step e). Reaction with activated heterocycles 7 ($R^{16}$ being e. g. a halide or a methanesulfonate) using sodium hydride or sodium, potassium or cesium carbonate in N,N-dimethylformamide, dimethylsulfoxide, dimethylacetamide or tetrahydrofuran, at a temperature ranging from 0° C. to 140° C., preferably at ambient temperature, leads to compounds 8 (step f). Alternatively, heterocycles 7 with $R^{16}$=OH can be transformed in situ to the corresponding triflate by treatment with trifluoromethanesulfonic anhydride/2,6-di-tert-butylpyridine in dichloromethane at 0° C. This triflate is then reacted with amines 5 in the presence of 2,6-di-tert-butylpyridine as base in nitromethane between ambient temperature and 60° C. to yield compounds 8 [following a procedure from Belostotskii, Anatoly M., Hassner, A., *Tetrahedron Lett.* 1994, 35(28), 5075–6] (step f). Further, steps d and f can be exchanged to synthesize compounds 8 for $R^{10}$≠hydrogen and steps f and c can be exchanged in order to synthesize compounds 8 with $R^{10}$ being equal to hydrogen. Secondary amines 8 ($R^{10}$=H) can be reductively methylated with an aqueous solution of $NaH_2PO_3$ and formaldehyde between ambient temperature and 65° C. [Loibner, H., Pruckner, A., Stuetz, A., *Tetrahedron Lett.* 1984, 25, 2535–2536] to give compounds 8 with $R^{10}$=Me. Ensuing hydrolysis with aqueous LiOH, NaOH or KOH in tetrahyrofuran/EtOH or another suitable solvent produces compounds 9 in the form of the free acid (step g). 2,3-Dihydroindole compounds 10 can be synthesized via partial reduction of indoles 8, e. g. by treating them with sodium cyano borohydride, preferably at ambient temperature in solvents like acetic acid or solvent mixtures like acetic acid/dichloromethane (step h). Dihydroindole esters 10 can optionally be hydrolyzed under the conditions given in step g to yield carboxylic acids 11 (step i). If the heterocyclic compounds 7 (prepared as described in schemes 5–8) and/or the aminoindoles 5 contain chiral centers, ester compounds 8 and 10 and carboxylic acids 9 and 11 are obtained as mixtures of diastereomers or enantiomers, which can be separated by methods well known in the art, e. g. (chiral) HPLC chromatography or crystallization. Racemic compounds can e. g. be separated into their antipodes via diastereomeric salts by crystallization with optically pure amines such as e. g. (R) or (S)-1-phenyl-ethylamine, (R) or (S)-1-naphthalen-1-yl-ethylamine, brucine, quinine or quinidine or by separation of the antipodes by specific chromatographic methods using either a chiral adsorbens or a chiral eluent.

6-Hydroxyindoles 1 (scheme 1) and O-protected 6-hydroxyindoles 2 (scheme 1) as we as their regioisomeric 4- and 5-hydroxyindole analogues are known or can be synthesized by methods known in the art. Examples for possible syntheses of these key intermediates (compounds 6 and 7 in scheme 4) are given in scheme 4 for $R^8$ in 1 being equal to hydroxy or protected hydroxy. Analogous key intermediates where $R^6$ or $R^7$ is equal to hydroxy or hydroxy carrying a protecting group can be synthesized applying the same reaction sequence.

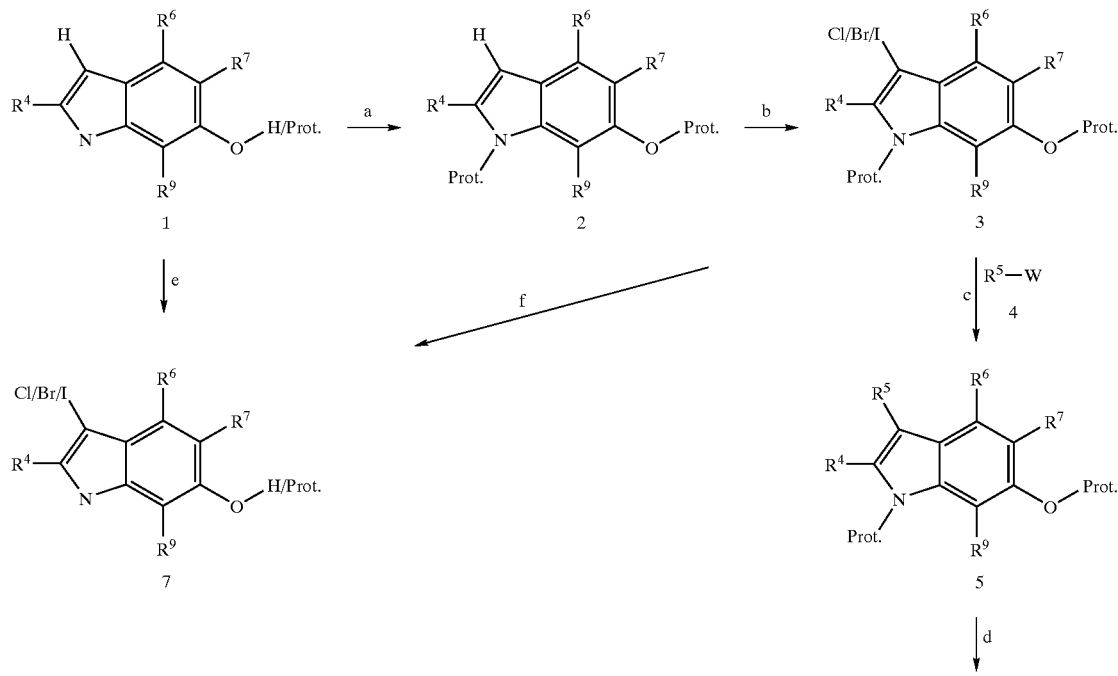

Scheme 4

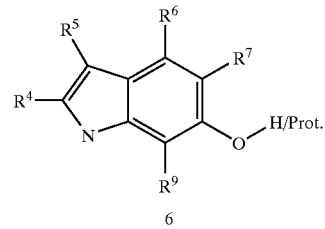

Introduction of a protecting group at the nitrogen atom of indoles 1 can be performed under standard conditions, e. g. by deprotonation with a base like n-butyllithium, preferably at −78° C., and subsequent addition of e. g. tert-butyldimethylsilyl chloride at temperatures between −78° C. and ambient temperature in solvents like tetrahydrofuran (step a). Halogenation of protected indoles 2, e. g. through reaction with N-bromosuccinimide at temperatures between −78° C. and ambient temperature in solvents like tetrahydrofuran delivers 3-halo indoles 3 (step b). Compounds 3 can—following halogen metal exchange, preferably with tert-butyllithium at −78° C. in solvents like tetrahydrofuran—be reacted with alkylating reagents 4 wherein W is a chlorine, bromine or iodine atom, preferably with alkyl iodides, at temperatures between −78° C. and ambient temperature in solvents like tetrahydrofuran, to form indoles 5 bearing a substituent in position 3 (step c). N-Deprotection or simultaneous N- and O-deprotection of compounds 5 leading to building blocks 6 can be performed by methods described in the literature, e. g. by treatment with tetrabutyl ammonium fluoride at temperatures between −15° C. and ambient temperature in a solvent like tetrahydrofuran, if the protecting groups are silyl ethers and/or silylated indoles (step d).

Building blocks 7 carrying a chlorine, bromine or iodine substituent in position 3 can be synthesized by halogenation of indoles 1, optionally carrying a protecting group at the hydroxy function, e. g. by reaction with N-chlorosuccinimide at temperatures between −15° C. and the reflux temperature of the solvent in solvents like dichloromethane or chloroform (step e). Alternatively, the same halo-indoles 7 can be obtained via N-deprotection or N- and O-deprotection of indoles 3 as described in step d (step f).

Heterocyclic compounds 6 (scheme 1), identical to compounds 2 (scheme 2) and compounds 7 (scheme 3) are known or can be synthesized by methods known in the art. Schemes 5 to 8 give representative examples for the synthesis of those key intermediates.

Scheme 5

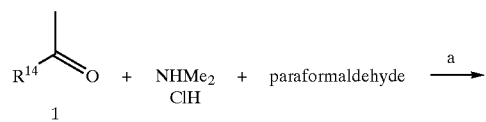

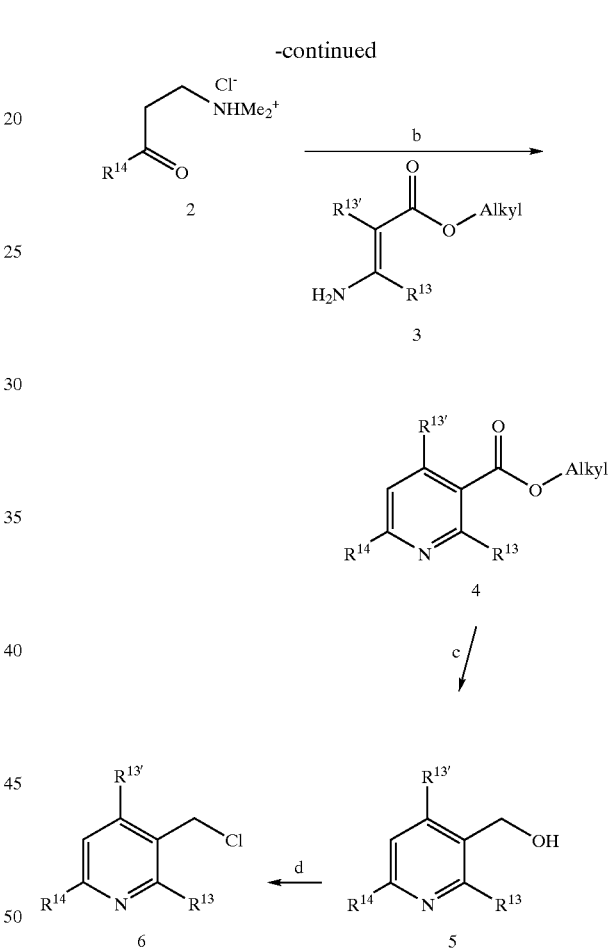

Pyridines 5 and 6 can be synthesized from ketones 1 (scheme 5). A mixture of ketones 1 with paraformaldehyde and dimethylamine hydrochloride in a solvent like ethanol in the presence of an acid like 37% HCl is heated under reflux for 2 to 10 hours to give amino-ketones 2 (step a). Reaction of compounds 2 with 3-amino-crotonic acid esters 3 in acetic acid at reflux temperature for 2 to 8 hours gives esters 4 (step b). Esters 4 can be reduced with diisobutylaluminium hydride solution (in toluene) at −30° C. to room temperature for 30 min to 3 h in solvents like tetrahydrofuran to give alcohols 5 (step c). Reaction of alcohols 5 with thionyl chloride in dichloromethane at 0° C. to room temperature for 5 min to 1 h gives access to chlorides 6 (step d).

Scheme 6

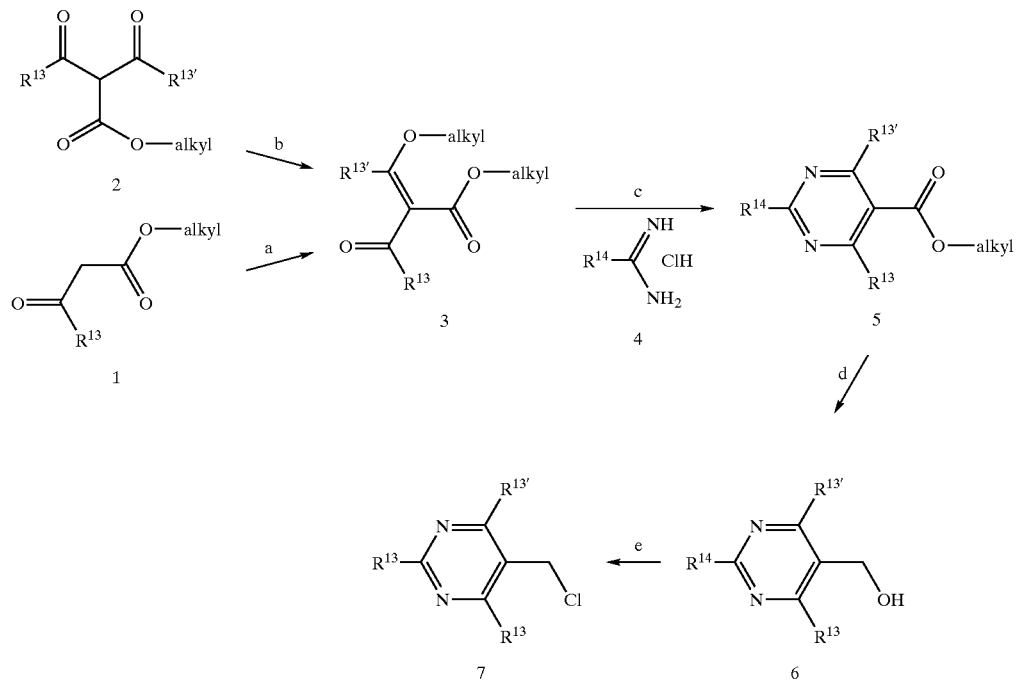

The synthesis of chlormethyl pyrimidines 7 and pyrimidine methanol compounds 6 is described in scheme 6. Reaction of 3-oxo-esters 1 with triethyl orthoformate in acetic anhydride at room temperature to reflux for 1 to 8 hours gives an E/Z mixture of the 3-ethoxy-acrylic acid esters 3 (step a). Diketo-esters 2 are reacted with methyl triflate in the presence of cesium carbonate in acetonitrile to give O-methylated products 3 (step b) [S. W. McCombie et al. Bioorganic & Medicinal Chemistry Letters 13 (2003) 567–571], thus yielding substituted enolethers 3 ($R^{13'}$ not H). Reaction with amidine hydrochlorides 4 in ethanol in the presence of alkali tert-butoxide at room temperature gives access to esters 5 (step c). Esters 5 can be reduced with diisobutylaluminium hydride solution (in toluene) at −30° C. to room temperature for 30 min to 3 h in solvents like tetrahydrofuran to give alcohols 6 (step d). Reaction of alcohols 6 with thionyl chloride in dichloromethane at 0° C. to room temperature for 5 min to 1 h gives access to chlorides 7 (step e).

Scheme 7

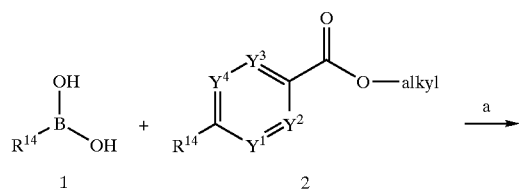

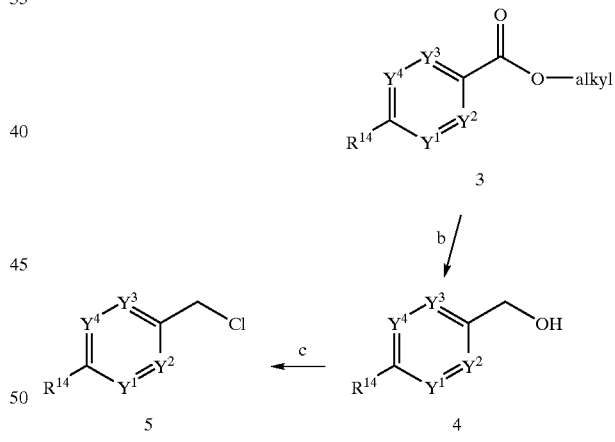

A general synthesis for alcohols 4 and chlorides 5 is depicted in scheme 7. Suzuki-coupling between boronic acides 1 and 6-halo-pyridazine-3-carboxylic acid esters 2,5-halo-pyrazine-2-carboxylic acid esters 2,6-halo-nicotinic acid esters 2,5-halo-pyridine-2-carboxylic acid esters 2,2-halo-pyrimidine-5-carboxylic acid esters 2 or 5-halo-pyrimidine-2-carboxylic acid esters 2 in the presence of $Pd(PPh_3)_4$ or $PdCl_2(dppf)$ [(1,1'-bis(diphenylphosphino)ferrocene)-dichloropalladium(II).$CH_2Cl_2$ (1:1)] in toluene, dimethoxyethane, ethanol or N,N-dimethylformamide with cesium carbonate, potassium carbonate or cesium fluoride at room temperature to 90° C. for 2 to 8 h give esters 3 (step a). Esters 2 are either commercially available or can be prepared by methods known to a person skilled in the art. Esters 3 can be reduced with diisobutylaluminium hydride solution (in toluene) at −30° C. to room temperature for 30 min to 3 h in solvents like tetrahydrofuran to give alcohols 4 (step b). Reaction of alcohols 4 with thionyl chloride in dichloromethane at 0° C. to room temperature for 5 min to 1 h gives access to chlorides 5 (step c).

pounds 5 which contain a chiral center can optionally be separated into optically pure antipodes by methods well known in the art, e. g. chromatography on a chiral HPLC column, or by derivatization with an optically pure acid to form esters, which can be separated by conventional HPLC chromatography and can then be converted back to the enantiomerically pure alcohols 5. The reduction of ketones

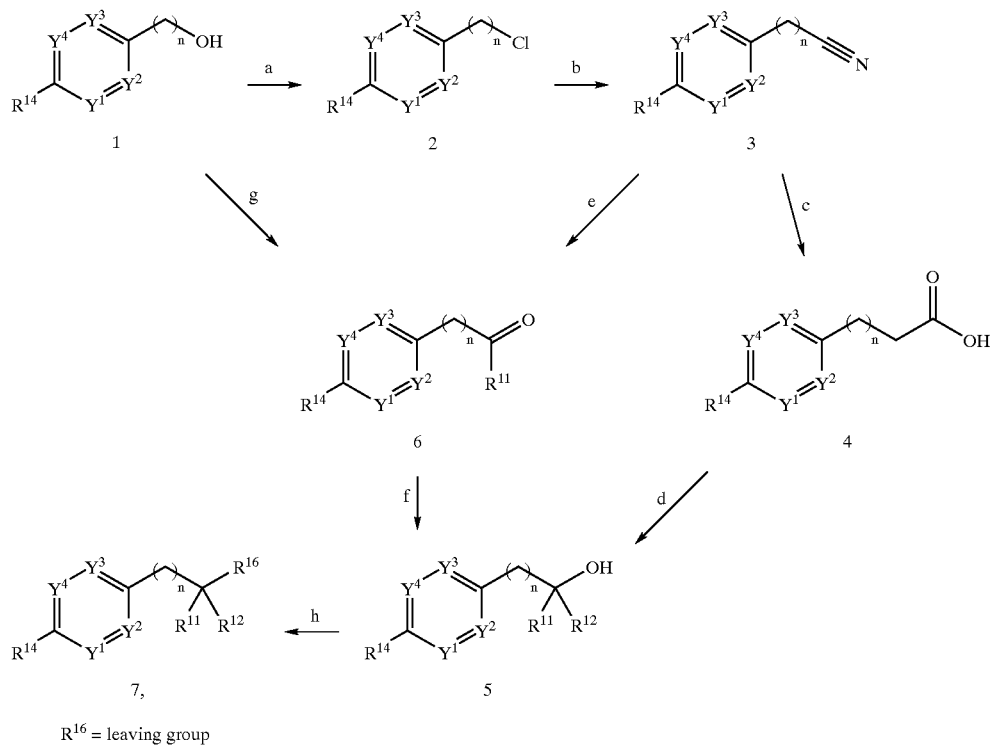

Scheme 8

$R^{16}$ = leaving group

Alcohols 1 in scheme 8 comprising a chain length n equal to one or two can be converted into analogues with a chain length of n+1 carbon atoms by methods well known in the art, e. g. by conversion of the primary alcohol 1 into a suitable leaving group, e. g. a halide 2 (step a), followed by reaction with cyanide to form nitriles 3 (step b) and saponification to acids 4 (step c). Acids 4 can be further transformed into the primary alcohols 5 ($R^{11}$=H, $R^{12}$=H), e. g. by using diborane in tetrahydrofuran (step d). Optionally, such alcohols 5 can be elongated to a chain length of n+1 carbon atoms by repeating the reaction sequence described for alcohols 1 to 5. In order to introduce substituents $R^{11}$ and/or $R^{12}$ different from hydrogen, cyano intermediates 3 can be reacted with alkyl Grignard reagents $R^{11}$MgX in solvents like ether or tetrahydrofuran between 0° C. and the reflux temperature of the solvent to form the corresponding $R^{11}$CO-alkyl ketones 6 (step e) or with diisobutylaluminium hydride to form the corresponding aldehydes 6 ($R^{11}$=H). Treatment of compounds 6 with an alkyllithium reagent $R^{12}$Li in solvents like ether or tetrahydrofuran gives alcohols 5 (step f); treatment of compounds 6 with lithium aluminium hydride in solvents like tetrahydrofuran or ether or with sodium borohydride in solvents like ethanol or methanol, preferably at temperatures between −15° C. and 40° C., gives alcohols 5 with $R^{12}$=H (step f). The alcohol com- 6 to the corresponding secondary alcohols 5 of scheme 8 can also be carried out in an enantioselective fashion leading to the (R)- or (S)-alcohols 5, e. g. by treatment with borane-dimethylsulfide complex and (S)- or (R)-2-methyl-CBS-oxazaborolidine as chiral catalyst in tetrahydrofuran, preferably at temperatures between −78° C. and ambient temperature, according to Corey et al. (E. J. Corey, R. K. Bakshi, S. Shibata, *J. Am. Chem. Soc.* 1987, 109, 5551–5553), or by treatment with (+)- or (−)-B-chlorodiisopinocampheyl-borane (DIP-Cl), according to Brown et al. (P. V. Ramachandran, B. Gong, A. V. Teodorovic, H. C. Brown, *Tetrahedron: Asymmetry* 1994, 5, 1061–1074). Aldehydes 6 ($R^{11}$=H, n=0) can also be synthesized from primary alcohols 1 by methods known in the art, e. g. by treatment with pyridinium chlorochromate in dichloromethane, preferably at temperatures between room temperature and the reflux temperature of dichloromethane, or by treatment with manganese dioxide in solvents like dichloromethane, preferably at room temperature (step g). These aldehydes 6 can be converted to the corresponding secondary alcohols 5 through reaction with alkyl organometallic compounds, preferably under the conditions discussed above. Finally, the alcohols 5 of scheme 8 can be converted into compounds of formula 7, e. g. by treatment with methanesulfonyl chloride in dichloromethane in the presence of a base like triethylamine preferably in a temperature range between −20° C. and room temperature or thionyl chloride in dichloromethane at 0° C. to room temperature or by reaction with carbon tetrachloride or carbon tetrabromide and triphenylphosphine in solvents like tetrahydrofuran preferably in a temperature range between room temperature and the reflux temperature of the solvents or by treatment with triflic anhydride, 2,6-lutidine and 4-dimethylaminopyridine in dichloromethane between −30° C. and room temperature; thus yielding compounds of formula 7 as methanesulfonates, triflates, chlorides or bromides, respectively (step h).

The following tests were carried out in order to determine the activity of the compounds of formula (I).

Background information on the performed assays can be found in: Nichols J S et al. "Development of a scintillation proximity assay for peroxisome proliferator-activated receptor gamma ligand binding domain", (1998) Anal. Biochem. 257:112–119.

Full-length cDNA clones for humans PPARδ and PPARα and mouse PPARγ were obtained by RT-PCR from human adipose and mouse liver cRNA, respectively, cloned into plasmid vectors and verified by DNA sequencing. Bacterial and mammalian expression vectors were constructed to produce glutathione-s-transferase (GST) and Gal4 DNA binding domain proteins fused to the ligand binding domains (LBD) of PPARδ (aa 139 to 442), PPARγ (aa 174 to 476) and PPARα (aa 167 to 469). To accomplish this, the portions of the cloned sequences encoding the LBDs were amplified from the full-length clones by PCR and then subcloned into the plasmid vectors. Final clones were verified by DNA sequence analysis.

Induction, expression, and purification of GST-LBD fusion proteins were performed in *E. coli* strain BL21 (pLysS) cells by standard methods (Ref: Current Protocols in Molecular Biology, Wiley Press, edited by Ausubel et al.).

Radioligand Binding Assay

PPARδ receptor binding was assayed in HNM10 (50 mM Hepes, pH 7.4, 10 mM NaCl, 5 mM $MgCl_2$, 0.15 mg/ml fatty acid-free BSA and 15 mM DTT). For each 96 well reaction a 500 ng equivalent of GST-PPARδ-LBD fusion protein and radioligand, e.g. 20000 dpm {2-methyl-4-[4-methyl-2-(4-trifluoromethyl-phenyl)-thiazol-5-yl-ditritiomethylsulfanyl]-phenoxy}-acetic acid, was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resuspended in 50 ul of HNM. Radioligand was added and the reaction incubated at RT for 1 h and scintillation proximity counting performed in the presence of test compounds was determined. All binding assays were performed in 96 well plates and the amount of bound ligand was measured on a Packard TopCount using OptiPlates (Packard). Dose response curves were done in triplicates within a range of concentration from $10^{-10}$ M to $10^{-4}$ M.

PPARα receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARα-LBD fusion protein was bound to 10 μg SPA beads (PharmaciaAmersham) in a final volume of 50 μl by shaking. The resulting slurry was incubated for 1 h at RT and centrifuged for 2 min at 1300 g. The supernatant containing unbound protein was removed and the semidry pellet containing the receptor-coated beads was resolved in 50 μl of TKE. For radioligand binding e.g. 10000 dpm of 2(S)-(2-benzoyl-phenylamino)-3-{4-[1,1-ditritio-2-(5-methyl-2-phenyl-oxazol-4-yl)-ethoxy]-phenyl}-propionic acid or 2,3-ditritio-2(S)-methoxy-3-{4-[2-(5-methyl-2-phenyl-oxazol-4-yl)-ethoxy]-benzo[b]thiophen-7-yl}-propionic acid in 50 ul were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

PPARγ receptor binding was assayed in TKE50 (50 mM Tris-HCl, pH 8, 50 mM KCl, 2 mM EDTA, 0.1 mg/ml fatty acid-free BSA and 10 mM DTT). For each 96 well reaction an 140 ng equivalent of GST-PPARγ-LBD fusion protein was bound to 10 μg SPA beads (PharmaciaAmersham) in a final volume of 50 ul by shaking. The resulting slurry was incubated for 1 h at RT and centrifuged for 2 min at 1300 g. The supernatant containing unbound protein was removed and the semidry pellet containing the receptor-coated beads was resolved in 50 ul of TKE. For radioligand binding e.g. 10000 dpm 2(S)-(2-benzoyl-phenylamino)-3-{4-[1,1-ditritio-2-(5-methyl-2-phenyl-oxazol-4-yl)-ethoxy]-phenyl}-propionic acid in 50 μl were added, the reaction incubated at RT for 1 h and scintillation proximity counting performed. All binding assays were performed in 96 well plates and the amount of bound ligand measured on a Packard TopCount using OptiPlates (Packard). Nonspecific binding was determined in the presence of $10^{-4}$ M unlabelled compound. Dose response curves were done in triplicates within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95%O2:5% $CO_2$ atmosphere. Cells were seeded in 6 well plates at a density of $10^5$ Cells/well and then batch-transfected with either the pFA-PPARδ-LBD, pFA-PPARγ-LBD or pFA-PPARα-LBD expression plasmids plus a reporter plasmid. Transfection was accomplished with the Fugene 6 reagent (Roche Molecular Biochemicals) according to the suggested protocol. Six hours following transfection, the cells were harvested by trypsinization and seeded in 96 well plates at a density of $10^4$ cells/well. After 24 hours to allow attachment of cells, the medium was removed and replaced with 100 ul of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) to lyse the cells and initiate the luciferase reaction was added. Luminescence for luciferase was measured in a Packard TopCount. Transcriptional activation in the presence of a test substance was expressed as fold-activation over cells incubated in the absence of the substance. EC50 values were calculated using the XLfit program (ID Business Solutions Ltd. UK).

The free acids of the compounds of the present invention ($R^1$ is hydrogen) exhibit $IC_{50}$ values of 0.5 nM to 10 μM, preferably 1 nM to 100 nM for PPARδ and $IC_{50}$ values of 1 nM to 10 μM, preferably 10 nM to 5 μM for PPARα. Compounds, in which $R^1$ is not hydrogen are converted in vivo to compounds in which $R^1$ is hydrogen. The following table shows measured values for some selected compounds of the present invention.

|  | PPARα<br>IC$_{50}$ (μmol/l) | PPARγ<br>IC$_{50}$ (μmol/l) | PPARδ<br>IC$_{50}$ (μmol/l) |
|---|---|---|---|
| Example 2 | 1.32 | >10 | 0.083 |
| Example 6 | 1.58 | >10 | 0.017 |
| Example 7 | 0.211 | >10 | 0.001 |

The compounds of formula (I) and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula (I) and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula (I) can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1–500 mg, preferably 0.5–100 mg, of a compound of formula (I).

The following examples serve to illustrate the present invention in more detail. They are, however, not intended to limit its scope in any manner.

EXAMPLES

Abbreviations:

AcOEt=ethyl acetate, AcOH=acetic acid, DIBALH=diisobutylaluminium hydride, DMF=N,N-dimethylformamide, EtOH=ethanol, eq.=equivalent(s), HPLC=high performance liquid chromatography, min.=minutes, mp.=melting point, quant.=quantitative, RT=room temperature, sat.=saturated, THF=tetrahydrofuran.

Example 1

{5-[4-(2-Methoxy-ethyl)-2-(4-trifluoromethyl-phenyl)-pyrimidin-5-ylmethoxy]-indol-1-yl}-acetic acid a] 5-(tert-Butyl-dimethyl-silanyloxy)-1H-indole A solution of 5 g (37.55 mmol) of 5-hydroxy-indole, 6.13 g (39.4 mmol) of tert-butyldimethylsilyl chloride and 5.37 g (68.1 mmol) of imidazole in 50 ml DMF was stirred for 20 h at RT. The reaction mixture was taken up in ether, washed with 1N HCl and water and the ether solution was then concentrated under reduced pressure, to give 9.4 g (quant.) of clean 5-(tert-butyl-dimethyl-silanyloxy)-1H-indole.

MS: 248.1 (M+H)$^+$.

b] [5-(tert-Butyl-dimethyl-silanyloxy)-indol-1-yl]-acetic acid ethyl ester

To a solution of 9.2 g (37.18 mmol) 5-(tert-butyl-dimethyl-silanyloxy)-1H-indole and 4.79 ml (40.9 mmol) ethyl bromoacetate in 140 ml of DMF was added 36.35 g (111.5 mmol) of cesium carbonate. The reaction mixture was stirred for 3 h at RT, taken up in ether and then washed with 1N HCl and water. The ether phase was concentrated under reduced pressure to give 12.93 g (quant.) of almost pure [5-(tert-butyl-dimethyl-silanyloxy)-indol-1-yl]-acetic acid ethyl ester.

MS: 334.1 (M+H)$^+$.

c] (5-Hydroxy-indol-1-yl)-acetic acid ethyl ester

To an ice cooled solution of 12.9 g (38.7 mmol) [5-(tert-butyl-dimethyl-silanyloxy)-indol-1-yl]-acetic acid ethyl ester in 130 ml of THF was added 12.45 g (38.7 mmol) of tetrabutylammonium fluoride hydrate. The reaction mixture was stirred for 1 h at RT, taken up in ether and washed with 1N HCl and water. Evaporation of the solvent under reduced pressure gave 7.07 g (83%) of pure (5-hydroxy-indol-1-yl)-acetic acid ethyl ester.

MS: 220.1 (M+H)$^+$.

d] 2-[1-Ethoxy-meth-(E,Z)-ylidene]-5-methoxy-3-oxo-pentanoic acid ethyl ester

A solution of 5.5 g (34.33 mmol) 5-methoxy-3-oxo-pentanoic acid methyl ester and 11.42 ml (68.67 mmol) triethyl orthoformate in 50 ml acetic anhydride was refluxed at 150° C. for 5 h. The reaction mixture was concentrated at 90° C. under reduced pressure to give 7.5 g of pure 2-[1-ethoxy-meth-(E,Z)-ylidene]-5-methoxy-3-oxo-pentanoic acid ethyl ester.

MS: 231.2 (M+H)$^+$.

e] 4-(2-Methoxy-ethyl)-2-(4-trifluoromethyl-phenyl)-pyrimidine-5-carboxylic acid ethyl ester To a solution of 6.02 g (23.1 mmol) 4-trifluoromethyl-benzamidine HCl in 50 ml ethanol was added 2.29 g (23.1 mmol) sodium tert-butoxide and 5 g (23.1 mmol) 2-[1-ethoxy-meth-(E,Z)-ylidene]-5-methoxy-3-oxo-pentanoic acid ethyl ester. The reaction mixture was stirred at RT over night and for 1 h at reflux temperature. After the solvent was removed under reduced pressure, the residue was taken up in ether and washed with 1N HCl and water. The crude product was purified by chromatography over silica gel with AcOEt/heptane 1:3 to provide 5.9 g pure 4-(2-methoxy-ethyl)-2-(4-trifluoromethyl-phenyl)-pyrimidine-5-carboxylic acid ethyl ester.

MS: 355.0 (M+H)$^+$.

f] [4-(2-Methoxy-ethyl)-2-(4-trifluoromethyl-phenyl)-pyrimidin-5-yl]-methanol

To a dry ice chilled solution of 4 g (11.29 mmol) 4-(2-methoxy-ethyl)-2-(4-trifluoromethyl-phenyl)-pyrimidine-5-carboxylic acid ethyl ester in 60 ml THF was dropped at −70° C. 28.22 ml (33.87 mmol) 1.2M DIBALH solution in toluene. The reaction mixture was stirred 1 h at −70° C. and then the reaction temperature was allowed to rise to RT and the reaction was stirred for further 2 h at RT. After dropwise addition of 100 ml 1N HCl to the reaction solution, it was partitioned between ether and water to provide, after concentration of the ether solution under reduced pressure, 3.58 g of pure [4-(2-methoxy-ethyl)-2-(4-trifluoromethyl-phenyl)-pyrimidin-5-yl]-methanol.

MS: 313.0 (M+H)$^+$.

g] 5-Chloromethyl-4-(2-methoxy-ethyl)-2-(4-trifluoromethyl-phenyl)-pyrimidine

A solution of 3.23 g (10.34 mmol) [4-(2-methoxy-ethyl)-2-(4-trifluoromethyl-phenyl)-pyrimidin-5-yl]-methanol and 0.788 ml (10.86 mmol) thionylchloride in 30 ml dichloromethane was stirred for 1 h at RT. The reaction mixture was taken up in ether and washed with sodium bicarbonate solution and water. The ether phase was concentrated under reduced pressure to give 3.42 g of pure 5-chloromethyl-4-(2-methoxy-ethyl)-2-(4-trifluoromethyl-phenyl)-pyrimidine.

h] {5-[4-(2-Methoxy-ethyl)-2-(4-trifluoromethyl-phenyl)-pyrimidin-5-ylmethoxy]-indol-1-yl}-acetic acid ethyl ester To a solution of 300 mg (0.91 mmol) 5-chloromethyl-4-(2-methoxy-ethyl)-2-(4-trifluoromethyl-phenyl)-pyrimidine and 199 mg (0.91 mmol) (5-hydroxy-indol-1-yl)-acetic acid ethyl ester in 5 ml DMF was added 443 mg (136 mmol) cesium carbonate. The reaction mixture was stirred at RT for 3 h and then taken up in ether, washed with 1N HCl and water. The crude product was purified by chromatography with AcOEt/heptane 1:4 to provide 152 mg of pure {5-[4-(2-methoxy-ethyl)-2-(4-trifluoromethyl-phenyl)-pyrimidin-5-ylmethoxy]-indol-1-yl}-acetic acid ethyl ester.

MS: 514.3 (M+H)$^+$.

i] {5-[4-(2-Methoxy-ethyl)-2-(4-trifluoromethyl-phenyl)-pyrimidin-5-ylmethoxy]-indol-1-yl}-acetic acid A solution of 147 mg (0.29 mmol) {5-[4-(2-methoxy-ethyl)-2-(4-trifluoromethyl-phenyl)-pyrimidin-5-ylmethoxy]-indol-1-yl}-acetic acid ethyl ester and 0.9 ml 1N lithium hydroxide solution in 1.5 ml THF were stirred over night at RT. The reaction mixture was partitioned between ether, 1N HCl and water. The residue was suspended in ether/heptane 1:9 and the resulting crystals were filtered off to give 118 mg of pure {5-[4-(2-methoxy-ethyl)-2-(4-trifluoromethyl-phenyl)-pyrimidin-5-ylmethoxy]-indol-1-yl}-acetic acid.

MS: 484.2 (M−H)$^-$.

Example 2

{5-[4-Methyl-2-(4-trifluoromethyl-phenyl)-pyrimidin-5-ylmethoxy]-indol-1-yl}-acetic acid a] 2-[1-Ethoxy-meth-(E,Z)-ylidene]-3-oxo-butyric acid ethyl ester A solution of 5 g (38.42 mmol) 3-oxo-butyric acid ethyl ester, 12.78 ml (76.84 mmol) triethyl orthoformate in 80 ml acetic anhydride was boiled for 2.5 h at 150° C. The reaction mixture was concentrated under reduced pressure at 90° C. to provide 6.84 g of almost pure 2-[1-ethoxy-meth-(E,Z)-ylidene]-3-oxo-butyric acid ethyl ester.

MS: 186.9 (M+H)$^+$.

b] 4-Methyl-2-(4-trifluoromethyl-phenyl)-pyrimidine-5-carboxylic acid ethyl ester To a solution of 2 g (7.67 mmol) 4-trifluoromethyl-benzamidine HCl in 30 ml ethanol was added 0.76 g (7.67 mmol) sodium tert-butoxide and 1.43 g (7.67 mmol) 2-[1-ethoxy-meth-(E,Z)-ylidene]-3-oxo-butyric acid ethyl ester. The reaction was stirred at RT over night and for 1 h under reflux. After the solvent was removed under reduced pressure, the residue was taken up in ether and washed with 1N HCl and water. The crude product was purified by chromatography over silica gel with AcOEt/heptane 1:3 to provide 1.7 g pure 4-methyl-2-(4-trifluoromethyl-phenyl)-pyrimidine-5-carboxylic acid ethyl ester.

MS: 311.0 (M+H)$^+$.

c] [4-Methyl-2-(4-trifluoromethyl-phenyl)-pyrimidin-5-yl]-methanol

To a dry ice chilled solution of 1.66 g (5.35 mmol) 4-methyl-2-(4-trifluoromethyl-phenyl)-pyrimidine-5-carboxylic acid ethyl ester in 20 ml THF was dropped at −70° C. 12.35 ml (16.05 mmol) 1.2M DIBALH solution in toluene. The reaction mixture was stirred 1 h at −70° C. and after attaining RT the reaction was stirred for another 2 h at this temperature. A solution of 50 ml of 1N HCl was added dropwise, then the reaction mixture partitioned between ether and water. The ether solution was concentrated under reduced pressure to provide 1.42 g of pure [4-methyl-2-(4-trifluoromethyl-phenyl)-pyrimidin-5-yl]-methanol.

MS: 269.2 (M+H)$^+$.

d] 5-Chloromethyl-4-methyl-2-(4-trifluoromethyl-phenyl)-pyrimidine

A solution of 1.33 g (4.96 mmol) [4-methyl-2-(4-trifluoromethyl-phenyl)-pyrimidin-5-yl]-methanol and 0.72 ml (9.92 mmol) thionylchloride in 30 ml dichloromethane was stirred for 1 h at RT. The reaction mixture was concentrated under reduced pressure to give 1.44 g of pure 5-chloromethyl-4-methyl-2-(4-trifluoromethyl-phenyl)-pyrimidine.

MS: 287.1 (M+H)$^+$.

e] 55 5-[4-Methyl-2-(4-trifluoromethyl-phenyl)-pyrimidin-5-ylmethoxy]-indol-1-yl)-acetic acid ethyl ester To a solution of 300 mg (0.94 mmol) 5-chloromethyl-4-methyl-2-(4-trifluoromethyl-phenyl)-pyrimidine and 206 mg (0.94 mmol) (5-hydroxy-indol-1-yl)-acetic acid ethyl ester (example 1 c]) in 3 ml DMF was added 375 mg (1.15 mmol) cesium carbonate. The reaction mixture was stirred for 3 h at RT and then partitioned between ether and water.

The crude product was purified by chromatography over silica gel with AcOEt/heptane 1.2 to give 194 mg of pure {5-[4-Methyl-2-(4-trifluoromethyl-phenyl)-pyrimidin-5-ylmethoxy]-indol-1-yl}-acetic acid ethyl ester.

MS: 470.2 (M+H)$^+$.

f] {5-[4-Methyl-2-(4-trifluoromethyl-phenyl)-pyrimidin-5-ylmethoxy]-indol-1-yl}-acetic acid 175 mg (0.37 mmol) {5-[4-methyl-2-(4-trifluoromethyl-phenyl)-pyrimidin-5-ylmethoxy]-indol-1-yl}-acetic acid ethyl ester and 0.75 ml 1N lithium hydroxide solution were stirred in 2 ml THF at RT for 2 h. The reaction mixture was taken up in ether and washed with 1N HCl and water. The crude product was suspended in ether/heptane 1:19 and the resulting crystals were filtered off to give 135 mg of pure {5-[4-methyl-2-(4-trifluoromethyl-phenyl)-pyrimidin-5-ylmethoxy]-indol-1-yl}-acetic acid.

MS: 440.1 (M–H)$^-$.

Example 3

{5-[4-Cyclopropyl-2-(4-trifluoromethyl-phenyl)-pyrimidin-5-ylmethoxy]-indol-1-yl}-acetic acid a] (E,Z)-2-Cyclopropanecarbonyl-3-ethoxy-acrylic acid methyl ester A solution of 10 g (70.34 mmol) 3-cyclopropyl-3-oxo-propionic acid methyl ester, 23.4 ml (140.68 mmol) of triethyl orthoformate in 100 ml acetic anhydride was refluxed at 150° C. for 5 h. The reaction mixture was concentrated at 95° C. under reduced pressure to give 14.35 g of crude (E,Z)-2-cyclopropanecarbonyl-3-ethoxy-acrylic acid methyl ester.

MS: 199.3 (M+H)$^+$.

b] 4-Cyclopropyl-2-(4-trifluoromethyl-phenyl)-pyrimidine-5-carboxylic acid ethyl ester To a solution of 4.74 g (18.19 mmol) 4-trifluoromethyl-benzamidine HCl in 50 ml of ethanol was added 1.82 g (18.19 mmol) of sodium tert-butoxide. After 2 min, 3.61 g of crude (E,Z)-2-cyclopropanecarbonyl-3-ethoxy-acrylic acid methyl ester was added and the reaction mixture was stirred over night at RT. The ethanol was removed under reduced pressure, the residue taken up in ether and washed with 1N HCl and water. The ether solution was concentrated under reduced pressure and the crude product purified by chromatography over silica gel with AcOEt/heptane 1:3 to give 4.25 g of pure 4-cyclopropyl-2-(4-trifluoromethyl-phenyl)-pyrimidine-5-carboxylic acid ethyl ester.

MS: 337.1 (M+H)$^+$.

c] [4-Cyclopropyl-2-(4-trifluoromethyl-phenyl)-pyrimidin-5-yl]-methanol

Within 10 min 31.6 ml (37.9 mmol) of a 1.2 M DIBALH solution in toluene were added dropwise to a dry ice cooled (–50° C.) solution of 4.25 g (12.64 mmol) 4-cyclopropyl-2-(4-trifluoromethyl-phenyl)-pyrimidine-5-carboxylic acid ethyl ester in 50 ml of THF. The reaction mixture was stirred 30 min at –50° C. and after letting rise the temperature to RT, for 1 h at RT. The reaction mixture was taken up in ether and washed with 1N HCl and water. The solvent was removed under reduced pressure to give 3.72 g of pure [4-cyclopropyl-2-(4-trifluoromethyl-phenyl)-pyrimidin-5-yl]-methanol.

MS: 295.1 (M+H)$^+$.

d] 5-Chloromethyl-4-cyclopropyl-2-(4-trifluoromethyl-phenyl)-pyrimidine

A mixture of 1.9 g (6.456 mmol) of [4-cyclopropyl-2-(4-trifluoromethyl-phenyl)-pyrimidin-5-yl]-methanol and 0.515 ml (7.1 mmol) thionylchloride in 20 ml dichloromethane was stirred for 1 h at RT. The reaction mixture was taken up in ether and washed with sodium bicarbonate solution and water. The ether phase was concentrated under reduced pressure to give 1.97 g of pure 5-chloromethyl-4-cyclopropyl-2-(4-trifluoromethyl-phenyl)-pyrimidine.

MS: 313.1 (M+H)$^+$.

e] {5-[4-Cyclopropyl-2-(4-trifluoromethyl-phenyl)-pyrimidin-5-ylmethoxy]-indol-1-yl}-acetic acid In analogy to the procedure described in example 1 h], 5-chloromethyl-4-cyclopropyl-2-(4-trifluoromethyl-phenyl)-pyrimidine was reacted with (5-hydroxy-indol-1-yl)-acetic acid ethyl ester (example 1 c]) in the presence of cesium carbonate to give {5-[4-cyclopropyl-2-(4-trifluoromethyl-phenyl)-pyrimidin-5-ylmethoxy]-indol-1-yl}-acetic acid ethyl ester, which was subsequently treated with lithium hydroxide in analogy to the procedure described in example 1 i] to yield {5-[4-cyclopropyl-2-(4-trifluoromethyl-phenyl)-pyrimidin-5-ylmethoxy]-indol-1-yl}-acetic acid.

MS: 468.5 (M+H)$^+$.

Example 4

(5-{Methyl-[4-methyl-2-(4-trifluoromethyl-phenyl)-pyrimidin-5-ylmethyl]-amino}-indol-1-yl)-acetic acid a] (1H-Indol-5-yl)-carbamic acid tert-butyl ester A solution of 5-amino indole (2 g, 15.2 mmol) and di-tert-butyl dicarbonate (3.49 g. 15.2 mmol) in dichloromethane (20 ml) was stirred at ambient temperature overnight. The reaction mixture was concentrated under reduced pressure to yield crude (1H-indol-5-yl)-carbamic acid tert-butyl ester (3.47 g) which was used in the next step without further purification.

MS: 250.3 (M+NH$_4$)$^+$.

b] (5-tert-Butoxycarbonylamino-indol-1-yl)-acetic acid ethyl ester

Cesium carbonate (7.17 g, 22 mmol) was added to a solution of 1H-indol-5-yl)-carbamic acid tert-butyl ester (3.39 g, 14.6 mmol) and bromo-acetic acid ethyl ester (2.38 ml, 20.3 mmol) in N,N-dimethyl formamide (30 ml). The reaction mixture was stirred at ambient temperature overnight, taken up in diethylether and washed with 1N HCl and water. The crude product was purified by chromatography over silica gel with AcOEt/heptane 1:3 to obtain (5-tert-butoxycarbonylamino-indol-1-yl)-acetic acid ethyl ester (1.6 g, 5.03 mmol, 34%).

MS: 319.4 (M+H)$^+$.

c] [5-(tert-Butoxycarbonyl-methyl-amino)-indol-1-yl]-acetic acid methyl ester and [5-(tert-butoxycarbonyl-methyl-amino)-indol-1-yl]-acetic acid ethyl ester To a ice cold solution of (5-tert-butoxycarbonylamino-indol-1-yl)-acetic acid ethyl ester (1.6 g, 5.03 mmol) and methyl iodide (0.41 ml, 6.53 mmol) in N,N-dimethyl formamide was added sodium hydride (55% in oil, 241 mg, 5.52 mmol). The reaction mixture was stirred at ambient temperature overnight. A second portion of methyl iodide (0.41 ml, 6.53 mmol) and sodium hydride (55% in oil, 241 mg, 5.52 mmol) was added. The reaction mixture was stirred another 4 h, taken up in diethylether and washed with water. The ether phase was concentrated under reduced pressure to provide a ~1:1 mixture of [5-(tert-butoxycarbonyl-methyl-amino)-indol-1-yl]-acetic acid methyl- and ethyl ester (1.7 g).

MS: 319.3 (M+H)$^+$, 333.5 (M+H)$^+$.

d] (5-Methylamino-indol-1-yl)-acetic acid methyl ester HCl-salt and (5-methylamino-indol-1-yl)-acetic acid ethyl ester HCl-salt A solution of a ~1:1 mixture of [5-(tert-butoxycarbonyl-methyl-amino)-indol-1-yl]-acetic acid methyl- and ethyl ester (1.7 g) and 4N HCl (10 ml) in dioxane was stirred for 30 min at ambient temperature. The reaction mixture was concentrated under reduced pressure. The residue was triturated with diethylether and dried in vacuo to give a mixture of (5-methylamino-indol-1-yl)-acetic acid methyl- and ethyl ester as their HCl-salts (1.29 g) as a brown foam.

MS: 219.3 (M+H)$^+$, 233.1 (M+H)$^+$.

e] (5-{Methyl-[4-methyl-2-(4-trifluoromethyl-phenyl)-pyrimidin-5-ylmethyl]-amino}-indol-1-yl)-acetic acid methyl ester To a solution of 320 mg (1.12 mmol) 5-chloromethyl-4-methyl-2-(4-trifluoromethyl-phenyl)-pyrimidine and 300 mg (1.12 mmol) (5-methylamino-indol-1-yl)-acetic acid methyl- and ethyl ester HCl salts in 4 ml DMF was added 107 mg (2.2 mmol) sodium hydride (55% in oil). The reaction mixture was stirred for 3 h at RT and then partitioned between 10% potassium hydrogen sulfate solution and water. The crude product was purified by chromatography over silica gel with AcOEt/heptane 1.2 to give 70 mg of pure (5-{methyl-[4-methyl-2-(4-trifluoromethyl-phenyl)-pyrimidin-5-ylmethyl]-amino}-indol-1-yl)-acetic acid methyl ester.

MS: 469 (M+H)$^+$.

f] (5-{Methyl-[4-methyl-2-(4-trifluoromethyl-phenyl)-pyrimidin-5-ylmethyl]-amino}-indol-1-yl)-acetic acid 70 mg (0.15 mmol) (5-{methyl-[4-methyl-2-(4-trifluoromethyl-phenyl)-pyrimidin-5-ylmethyl]-amino}-indol-1-yl)-acetic acid methyl ester and 0.3 ml 1N lithium hydroxide solution were stirred for 2 h in 0.5 ml THF at RT. To the reaction mixture was added 0.6 ml 1N HCl and then the mixture was taken up in AcOEt and washed with water. The crude product was suspended in ether/heptane 1:19. The resulting crystals were filtered off to provide 47 mg of pure (5-{methyl-[4-methyl-2-(4-trifluoromethyl-phenyl)-pyrimidin-5-ylmethyl]-amino}-indol-1-yl)-acetic acid.

MS: 453.2 (M−H)$^-$.

Example 5

{6-[2-Methyl-6-(4-trifluoromethyl-phenyl)-pyridin-3-ylmethoxy]-indol-1-yl}-acetic acid a] [6-(tert-Butyl-dimethyl-silanyloxy)-indol-1-yl]-acetic acid tert-butyl ester In analogy to the procedure described in example 1 b], 6-(tert-butyl-dimethyl-silanyloxy)-1H-indole was reacted with bromo-acetic acid tert-butyl ester in the presence of cesium carbonate to obtain [6-(tert-butyl-dimethyl-silanyloxy)-indol-1-yl]-acetic acid tert-butyl ester as colorless liquid.

MS: 362.4 (M+H)$^+$.

b] (6-Hydroxy-indol-1-yl)-acetic acid tert-butyl ester

In analogy to the procedure described in example 1 c], [6-(tert-butyl-dimethyl-silanyloxy)-indol-1-yl]-acetic acid tert-butyl ester was treated with tetrabutylammonium fluoride hydrate to obtain (6-hydroxy-indol-1-yl)-acetic acid tert-butyl ester as yellowish oil.

MS: 265.5 (M+NH$_4$)$^+$, 248.4 (M+H)$^+$.

c] 3-Dimethylamino-1-(4-trifluoromethyl-phenyl)-propan-1-one hydrochloride 4-(Trifluoromethyl) acetophenone (4.97 g, 26.4 mmol), paraformaldehyde (1.586 g, 2 eq.), dimethylamine hydrochloride (3.23 g, 1.5 eq.) were mixed together in 7 ml of EtOH, treated with 0.08 ml of 37% HCl, and heated to reflux for 5 h. Cooling down to ambient temperature, filtration and washing with tiny amounts of cold EtOH delivered 4.59 g of the title compound as white crystals, mp. 128–142° C. (dec.).

MS: 246.3 (M+H)$^+$.

d] 2-Methyl-6-(4-trifluoromethyl-phenyl)-nicotinic acid methyl ester 4.59 g (16.3 mmol) of the above prepared 3-dimethylamino-1-(4-trifluoromethyl-phenyl)-propan-1-one hydrochloride and 1.86 g (1.0 eq.) of 3-aminocrotonic acid methyl ester were dissolved in 50 ml of AcOH and heated to reflux for 4 h. After cooling, the bulk of the solvent was evaporated in vacuum, the residue dissolved in AcOEt, and washed with water and brine. Drying over sodium sulfate, evaporation of the solvents and flash chromatography (SiO$_2$, hexane/AcOEt=8/2) delivered finally 2.40 g of the title compound as light yellow waxy solid.

MS: 296.1 (M+H)$^+$.

e] [2-Methyl-6-(4-trifluoromethyl-phenyl)-pyridin-3-yl]-methanol g (3.39 mmol) of 2-methyl-6-(4-trifluoromethyl-phenyl)-nicotinic acid methyl ester in 7 ml of abs. THF were cooled down to 0° C. and reacted with 7.06 ml of DIBAL-H solution (1.2 M in toluene, 2.5 eq.) for 1 h. Careful quenching with ice/NH$_4$Cl, twofold extraction with AcOEt, washing with brine, drying over sodium sulfate, and evaporation of the solvents left a crude product which was purified by flash chromatography (SiO$_2$, hexane/AcOEt=7/3) to deliver 0.875 g of the title compound as off-white solid, mp. 76–78° C.

MS: 268.1 (M+H)$^+$.

f] {6-[2-Methyl-6-(4-trifluoromethyl-phenyl)-pyridin-3-ylmethoxy]-indol-1-yl}-acetic acid tert-butyl ester To an ice cold solution of (6-hydroxy-indol-1-yl)-acetic acid tert-butyl ester (70 mg, 0.28 mmol), [2-methyl-6-(4-trifluoromethyl-phenyl)-pyridin-3-yl]-methanol (76 mg, 0.28 mmol) and tributylphosphine (110 µl, 0.42 mmol) in tetrahydrofuran (4 ml) was added N,N,N',N'-tetramethyl azodicarboxamide (73 mg, 0.42 mmol) under an argon atmosphere. The cooling bath was removed and stirring continued for 14 h. Filtration over celite and evaporation of the solvent under reduced pressure gave a yellow oil which was purified by column chromatography (silica gel, heptane/AcOEt) to give 105 mg (0.21 mmol, 75%) of the title compound as white crystals.

MS: 497.3 (M+H)$^+$.

g] {6-[2-Methyl-6-(4-trifluoromethyl-phenyl)-pyridin-3-ylmethoxy]-indol-1-yl}-acetic acid To a solution of {6-[2-methyl-6-(4-trifluoromethyl-phenyl)-pyridin-3-ylmethoxy]-indol-1-yl}-acetic acid tert-butyl ester (20 mg, 0.04 4 µmol) in THF/methanol 2/1 (3 ml) was added a 1 N aqueous LiOH solution (1 ml). The reaction mixture was stirred for 14 h at ambient temperature, neutralized with 1 N aqueous HCl solution under ice cooling and concentrated under reduced pressure. The residue was dissolved in 1 N HCl/ice water 1/1 and ethyl acetate, the layers were separated and the aqueous layer was extracted with ethyl acetate. The combined organic layers were washed with ice water/brine 1/1, dried over sodium sulfate and the solvent was evaporated in vacuo to give the title compound (18 mg, 0.04 µmol, quant.) as white solid.

MS: 439.3 (M–H)⁻.

Example 6

{6-[2-Methyl-6-(4-trifluoromethyl-phenyl)-pyridin-3-ylmethoxy]-2,3-dihydro-indol-1-yl}-acetic acid a] [6-(tert-Butyl-dimethyl-silanyloxy)-indol-1-yl]-acetic acid ethyl ester To an ice cold solution of 6-(tert-butyl-dimethyl-silanyloxy)-1H-indole (1 g, 4.04 mmol) and cesium carbonate (1.45 g, 4.45 mmol) in DMF (10 ml) under an argon atmosphere was added bromo-acetic acid ethyl ester (490 µl, 4.45 mmol). The mixture was naturally warmed to room temperature, stirred for 14 h, poured onto 1 N HCl/ice water 1/1 and extracted two times with ethyl acetate. The combined organic layers were washed with water and dried over sodium sulfate. The solvent was removed under reduced pressure and the residue purified by column chromatography (silica gel, heptane/AcOEt) to give 1.2 g (3.6 mmol, 89%) of the title compound as yellow oil.

MS: 334.3 (M+H)⁺.

b] (6-Hydroxy-indol-1-yl)-acetic acid ethyl ester

To an ice cold solution of [6-(tert-butyl-dimethyl-silanyloxy)-indol-1-yl]-acetic acid ethyl ester (1.15 g, 3.45 mmol) in THF (11.5 ml) was added a 1 M solution of tetrabutylammonium fluoride in THF (3.45 ml, 3.45 mmol) within 15 min. The reaction mixture was stirred for 1 h at ambient temperature, poured onto 1 N HCl/ice water 1/1 and extracted two times with ethyl acetate. The combined organic layers were washed with brine/ice water 1/1 and dried over sodium sulfate. The solvent was removed under reduced pressure and the residue purified by column chromatography (silica gel, heptane/AcOEt) to give 590 mg (2.7 mmol, 78%) of the title compound as colorless crystals.

MS: 219.0 (M)⁺, 146.0.

c] {6-[2-Methyl-6-(4-trifluoromethyl-phenyl)-pyridin-3-ylmethoxy]-indol-1-yl}-acetic acid ethyl ester In analogy to the procedure described in example 5 f], (6-hydroxy-indol-1-yl)-acetic acid ethyl ester was reacted with [2-methyl-6-(4-trifluoromethyl-phenyl)-pyridin-3-yl]-methanol (example 5 e]) in the presence of tributylphosphine and N,N,N',N'-tetramethyl azodicarboxamide to yield {6-[2-methyl-6-(4-trifluoromethyl-phenyl)-pyridin-3-ylmethoxy]-indol-1-yl}-acetic acid ethyl ester as colorless crystals.

MS: 497.3 (M+H)⁺.

d] {6-[2-Methyl-6-(4-trifluoromethyl-phenyl)-pyridin-3-ylmethoxy]-2,3-dihydro-indol-1-yl}-acetic acid ethyl ester To a 10° C. cold solution of {6-[2-methyl-6-(4-trifluoromethyl-phenyl)-pyridin-3-ylmethoxy]-indol-1-yl}-acetic acid ethyl ester (17 mg, 0.036 µmol) in acetic acid (0.5 ml) was added sodium cyanoborohydride (14 mg, 0.22 µmol). The reaction mixture was naturally warmed to ambient temperature, stirred for 4 h and poured onto ice water/brine/ AcOEt 1/1/2. The layers were separated and the aqueous layer was extracted with ethyl acetate. The combined organic layers were washed with sat. sodium bicarbonate solution/brine 1/1 and brine/ice water 1/1 and dried over sodium sulfate. The solvent was removed under reduced pressure to give 17 mg (0.036 µmol, quant.) of the title compound as colorless crystals.

MS: 471.1 (M+H)⁺.

e] {6-[2-Methyl-6-(4-trifluoromethyl-phenyl)-pyridin-3-ylmethoxy]-2,3-dihydro-indol-1-yl}-acetic acid In analogy to the procedure described in example 5 g], {6-[2-methyl-6-(4-trifluoromethyl-phenyl)-pyridin-3-ylmethoxy]-2,3-dihydro-indol-1-yl}-acetic acid ethyl ester was treated with LiOH to obtain {6-[2-methyl-6-(4-trifluoromethyl-phenyl)-pyridin-3-ylmethoxy]-2,3-dihydro-indol-1-yl}-acetic acid as colorless crystals.

MS: 443.0 (M+H)⁺.

Example 7

{6-[4-Cyclopropyl-2-(4-trifluoromethyl-phenyl)-pyrimidin-5-ylmethoxy]-indol-1-yl}-acetic acid a] {6-[4-Cyclopropyl-2-(4-trifluoromethyl-phenyl)-pyrimidin-5-ylmethoxy]-indol-1-yl}-acetic acid ethyl ester A mixture of (6-hydroxy-indol-1-yl)-acetic acid ethyl ester (example 6 b]; 50 mg, 0.23 µmol), 5-chloromethyl-4-cyclopropyl-2-(4-trifluoromethyl-phenyl)-pyrimidine (example 3 d]; 78 mg, 0.25 µmol), cesium carbonate (82 mg, 0.25 µmol) and a trace of potassium iodide were suspended in acetone (5 ml). The suspension was stirred at ambient temperature for 72 h, the solvent was evaporated under reduced pressure and the residue dissolved in 1 N HCl/ice water 1/1 and ethyl acetate. The layers were separated and the aqueous layer was extracted with ethyl acetate. The combined organic layers were washed two times with brine/ice water 1/1 and dried over sodium sulfate. The solvent was removed under reduced pressure and the residue purified by column chromatography (silica gel, heptane/AcOEt) to give 71 mg (0.14 µmol, 63%) of the title compound as colorless crystals.

MS: 496.0 (M+H)⁺.

b] {6-[4-Cyclopropyl-2-(4-trifluoromethyl-phenyl)-pyrimidin-5-ylmethoxy]-indol-1-yl}-acetic acid In analogy to the procedure described in example 5 g], {6-[4-cyclopropyl-2-(4-trifluoromethyl-phenyl)-pyrimidin-5-ylmethoxy]-indol-1-yl}-acetic acid ethyl ester was treated with LiOH to obtain {6-[4-cyclopropyl-2-(4-trifluoromethyl-phenyl)-pyrimidin-5-ylmethoxy]-indol-1-yl}-acetic acid as colorless crystals.

MS: 466.0 (M–H)⁻.

Example 8

(6-{2-[2-Methyl-6-(4-trifluoromethyl-phenyl)-pyridin-3-yl]-ethoxy}-indol-1-yl)-acetic acid a] 3-Chloromethyl-2-methyl-6-(4-trifluoromethyl-phenyl)-pyridine To a suspension of [2-methyl-6-(4-trifluoromethyl-phenyl)-pyridin-3-yl]-methanol (26.7 g; 100 mmol; example 5 e]) in dichloromethane (100 ml), was added at 0° C. 10.9 ml (150 mmol) of thionyl chloride within 0.5 hours. Stirring was continued at ambient temperature for 1 hour. Afterwards, ice water was added and the mixture was stirred vigorously. Then, the layers were separated, the aqueous phase was extracted with 100 ml of dichloromethane. The combined organic phases were washed with water, aqueous sodium hydrogen carbonate, brine, and dried with anhydrous sodium sulfate. After evaporation, 27.9 g (97.6%) of 3-chloromethyl-2-methyl-6-(4-trifluoromethyl-phenyl)-pyridine were obtained as a light brown solid.

MS: 285.0 (M)$^+$.

b] [2-Methyl-6-(4-trifluoromethyl-phenyl)-pyridin-3-yl]-acetonitrile 27.2 g of 3-chloromethyl-2-methyl-6-(4-trifluoromethyl-phenyl)-pyridine (95.2 mmol) were dissolved in 100 ml of dimethyl sulfoxide; 5.9 g of sodium cyanide (120 mmol) were added and the mixture was stirred at room temperature for 18 hours. Then, the reaction mixture was poured into a mixture of ice and water and was subsequently extracted with 3 portions of 400 ml of tert-butyl methyl ether. The combined organic phases were washed with water, then with brine and dried with anhydrous sodium sulfate. After evaporation of the solvent, 25.2 g (95.8% of theory) of [2-methyl-6-(4-trifluoromethyl-phenyl)-pyridin-3-yl]-acetonitrile were obtained as a pale yellow solid.

MS: 276.1 (M)$^+$.

c] [2-Methyl-6-(4-trifluoromethyl-phenyl)-pyridin-3-yl]-acetic acid

A mixture of 25 g (90 mmol) of the above prepared [2-methyl-6-(4-trifluoromethyl-phenyl)-pyridin-3-yl]-acetonitrile, 20 g of sodium hydroxide (500 mmol), 60 ml of water and 250 ml of propanol was stirred vigorously at 100° C. Hydrolysis was complete after 2 hours. The reaction mixture was then evaporated to dryness and the residue was dissolved in 70 ml of water; then, 60 ml of cold 8 N aqueous HCl were added and the compound was extracted with three portions of 250 ml of ethyl acetate; the combined organic phases were washed with water and brine, dried with anhydrous sodium sulfate and evaporated. 25.1 g (93.9%) of [2-methyl-6-(4-trifluoromethyl-phenyl)-pyridin-3-yl]-acetic acid were obtained as a pale yellow solid.

MS: 296.0 (M+H)$^+$.

d] [2-Methyl-6-(4-trifluoromethyl-phenyl)-pyridin-3-yl]-acetic acid methyl ester A solution of 2.55 g (8.63 mmol) of [2-methyl-6-(4-trifluoromethyl-phenyl)-pyridin-3-yl]-acetic acid in 25 ml of methanol was cooled to −10° C.; 1.88 ml (25.9 mmol) of thionyl chloride were added. The reaction mixture was then stirred at ambient temperature for 2 hours. Subsequently, the solution was stirred with ice water, then extracted with three portions of 50 ml of tert.-butyl methyl ether. The combined organic layers were washed with water, aqueous sodium hydrogen carbonate, brine and dried on anhydrous sodium sulfate. After evaporation of the solvent, 2.6 g (97.3%) of the title compound were obtained as light brown solid.

MS: 309.1 (M)$^+$.

e] 2-[2-Methyl-6-(4-trifluoromethyl-phenyl)-pyridin-3-yl]-ethanol 2.6 g (8.40 mmol) of [2-methyl-6-(4-trifluoromethyl-phenyl)-pyridin-3-yl]-acetic acid methyl ester in 15 ml of dry tetrahydrofuran were added under an argon atmosphere within 15 minutes to a stirred suspension of 0.38 g (10 mmol) of lithium aluminium hydride in 5 ml of tetrahydrofuran. The reaction was exothermic. Subsequently, the mixture was stirred at room temperature for 1 hour. Then, 1 ml of ethyl acetate was dropped to the reaction mixture, followed by water, drop after drop, under argon, with stirring and cooling until the gas evolution ceased. The reaction mixture was diluted with 50 ml of ethyl acetate, dried with anhydrous sodium sulfate and filtered. The filtrate was evaporated and the residue was chromatographed on silicagel with a mixture of dichloromethane and tert.-butyl methyl ether (4:1 vol./vol.) as eluent. 1.88 g (79.5% of theory) of 2-[2-methyl-6-(4-trifluoromethyl-phenyl)-pyridin-3-yl]-ethanol was obtained as white solid.

MS: 281.1 (M)$^+$.

f] (6-{2-[2-Methyl-6-(4-trifluoromethyl-phenyl)-pyridin-3-yl]-ethoxy}-indol-1-yl)-acetic acid tert-butyl ester In analogy to the procedure described in example 5 f], (6-hydroxy-indol-1-yl)-acetic acid tert-butyl ester (example 5 b]) was reacted with 2-[2-methyl-6-(4-trifluoromethyl-phenyl)-pyridin-3-yl]-ethanol in the presence of di-tert-butyl azodicarboxylate and triphenylphosphine in tetrahydrofuran to yield (5-{2-[2-methyl-6-(4-trifluoromethyl-phenyl)-pyridin-3-yl]-ethoxy}-indol-1-yl)-acetic acid tert-butyl ester as colorless liquid.

MS: 511.3 (M+H)$^+$.

g] (6-{2-[2-Methyl-6-(4-trifluoromethyl-phenyl)-pyridin-3-yl]-ethoxy}-indol-1-yl)-acetic acid In analogy to the procedure described in example 5 g], (5-{2-[2-methyl-6-(4-trifluoromethyl-phenyl)-pyridin-3-yl]-ethoxy}-indol-1-yl)-acetic acid tert-butyl ester was treated with LiOH to obtain (5-{2-[2-methyl-6-(4-trifluoromethyl-phenyl)-pyridin-3-yl]-ethoxy}-indol-1-yl)-acetic acid as light brown solid.

MS: 453.5 (M−H)$^-$.

Example 9

{6-[6-(4-Trifluoromethoxy-phenyl)-pyridin-3-yl-methoxy]-indol-1-yl}-acetic acid a] [6-(4-Trifluoromethoxy-phenyl)-pyridin-3-yl]-methanol 6-(4-Trifluoromethoxy-phenyl)-pyridine-3-carbaldehyde (2.0 g, 7.48 mmol) was dissolved in EtOH (37 ml) and treated at 0° C. with NaBH$_4$ (0.28 g, 7.48 mmol). After 10 min the cooling bath was removed and stirring was continued at ambient temperature. Pouring onto crashed ice, twofold extraction with AcOEt, washing with water, drying over sodium sulfate, and evaporation of the solvents afforded 2.08 g (7.7 mmol, quant.) of the title compound as off-white solid of mp. 57–58° C.

MS: 269.1 (M)$^+$.

b] 5-Chloromethyl-2-(4-trifluoromethoxy-phenyl)-pyridine

[6-(4-Trifluoromethoxy-phenyl)-pyridin-3-yl]-methanol (0.40 g, 1.49 mmol) was dissolved in CH$_2$Cl$_2$ (7.2 ml) and treated dropwise at 0° C. with SOCl$_2$ (0.22 ml, 2 eq.). The reaction mixture was kept at 0° C. for 5 min and at RT for 30 min. Pouring onto crashed ice/NaHCO$_3$, twofold extraction with AcOEt, washing with water, drying over sodium sulfate, and evaporation of the solvents produced 0.419 g (1.46 mmol, 98%) of the title compound as off-white solid of mp. 34–36° C.

MS: 288.1, 290.1 (M+H)$^+$.

c] {6-[6-(4-Trifluoromethoxy-phenyl)-pyridin-3-yl-methoxy]-indol-1-yl}-acetic acid tert-butyl ester In analogy to the procedure described in example 7 a], (6-hydroxy-indol-1-yl)-acetic acid tert-butyl ester (example 5 b]) was reacted with 5-chloromethyl-2-(4-trifluoromethoxy-phenyl)-pyridine in the presence of cesium carbonate and potassium iodide, using acetonitrile as solvent, to obtain the title compound as colorless crystals.

d] {6-[6-(4-Trifluoromethoxy-phenyl)-pyridin-3-yl-methoxy]-indol-1-yl}-acetic acid In analogy to the procedure described in example 5 g], {6-[6-(4-trifluoromethoxy-phenyl)-pyridin-3-ylmethoxy]-indol-1-yl}-acetic acid tert-butyl ester was treated with LiOH to obtain the title compound as yellow crystals.

MS: 441.4 (M–H)⁻.

Example 10

{6-[2-Methyl-6-(3-trifluoromethyl-phenyl)-pyridin-3-ylmethoxy]-indol-1-yl}-acetic acid a] [2-Methyl-6-(3-trifluoromethyl-phenyl)-pyridin-3-yl]-methanol was prepared in analogy to examples 5 c] to 5 e], but starting the whole reaction sequence with 3-(trifluoromethyl) acetophenone instead of 4-(trifluoromethyl) acetophenone, to give the title compound as white crystals of mp. 73–75° C.

b] {6-[2-Methyl-6-(3-trifluoromethyl-phenyl)-pyridin-3-ylmethoxy]-indol-1-yl}-acetic acid ethyl ester In analogy to the procedure described in example5 f], (6-hydroxy-indol-1-yl)-acetic acid ethyl ester (example 6 b]) was reacted with [2-methyl-6-(3-trifluoromethyl-phenyl)-pyridin- 3-yl]-methanol in the presence of tributylphosphine and N,N,N',N'-tetramethyl azodicarboxamide to yield the title compound as colorless crystals.

MS: 469.1 (M+H)⁺.

c] {6-[2-Methyl-6-(3-trifluoromethyl-phenyl)-pyridin-3-ylmethoxy]-indol-1-yl}-acetic acid In analogy to the procedure described in example 5 g], {6-[2-methyl-6-(3-trifluoromethyl-phenyl)-pyridin-3-ylmethoxy]-indol-1-yl}-acetic acid ethyl ester was treated with LiOH to obtain the title compound as off-white crystals.

MS: 439.4 (M–H)⁻.

Example 11

(4-{2-[2-Methyl-6-(4-trifluoromethyl-phenyl)-pyridin-3-yl]-ethoxy}-indol-1-yl)-acetic acid a] [4-(tert-Butyl-dimethyl-silanyloxy)-indol-1-yl]-acetic acid ethyl ester In analogy to the procedure described in example 6 a], 4-(tert-butyl-dimethyl-silanyloxy)-1H-indole (EP 206225 A2) was reacted with bromo-acetic acid ethyl ester in the presence of cesium carbonate to obtain the title compound as yellow oil.

b] (4-Hydroxy-indol-1-yl)-acetic acid ethyl ester

In analogy to the procedure described in example 6 b], [4-(tert-butyl-dimethyl-silanyloxy)-indol-1-yl]-acetic acid ethyl ester was treated with tetrabutylammonium fluoride hydrate to obtain (4-hydroxy-indol-1-yl)-acetic acid ethyl ester as yellow oil.

MS: 220.4 (M+H)⁺.

c] (4-{2-[2-Methyl-6-(4-trifluoromethyl-phenyl)-pyridin-3-yl]-ethoxy}-indol-1-yl)-acetic acid ethyl ester In analogy to the procedure described in example 5 f], (4-hydroxy-indol-1-yl)-acetic acid ethyl ester was reacted with 2-[2-methyl-6-(4-trifluoromethyl-phenyl)-pyridin-3-yl]-ethanol (example 8 e]) in the presence of di-tert-butyl azodicarboxylate and triphenylphosphine in tetrahydrofuran to yield the title compound as white solid.

MS: 483.3 (M+H)⁺.

d] (4-{2-[2-Methyl-6-(4-trifluoromethyl-phenyl)-pyridin-3-yl]-ethoxy}-indol-1-yl)-acetic acid In analogy to the procedure described in example 5 g], (4-{2-[2-methyl-6-(4-trifluoromethyl-phenyl)-pyridin-3-yl]-ethoxy}-indol-1-yl)-acetic acid ethyl ester was treated with LiOH to obtain the title compound as white solid.

MS: 453.2 (M–H)⁻.

Example 12

{6-[4-(2-Methoxy-ethyl)-2-(6-trifluoromethyl-pyridin-3-yl)-pyrimidin-5-ylmethoxy]-indol-1-yl}-acetic acid a] (E,Z)-2-[1-Ethoxy-methylidene]-5-methoxy-3-oxo-pentanoic acid methyl ester A solution of 5-methoxy-3-oxovaleric acid methyl ester (21.96 g, 116.5 mmol) and triethyl orthoformate (35.3 ml, 233.1 mmol) in acetic anhydride (240 ml) was heated under reflux conditions for 2.5 h. The reaction mixture was concentrated under reduced pressure at 50° C. to give 29.06 g (134 mmol, quant.) of crude (E,Z)-2-[1-ethoxy-methylidene]-5-methoxy-3-oxo-pentanoic acid methyl ester.

MS: 217.2 (M+H)⁺.

b] 4-(2-Methoxy-ethyl)-2-(6-trifluoromethyl-pyridin-3-yl)-pyrimidine-5-carboxylic acid methyl ester and 4-(2-methoxy-ethyl)-2-(6-trifluoromethyl-pyridin-3-yl)-pyrimidine-5-carboxylic acid ethyl ester Sodium tert-butoxide (7.61 g, 96.1 mmol) was added to a solution of 6-(trifluoromethyl)pyridine-3-benzamidine HCl (16.24 g, 72 mmol) in ethanol (200 ml). After 5 min a solution of crude (E,Z)-2-[1-ethoxy-methylidene]-5-methoxy-3-oxo-pentanoic acid methyl ester (15.57 g, 72 mmol) in ethanol (70 ml) was added. The reaction mixture was stirred over night at 90° C. The ethanol was removed partially under reduced pressure, the residue diluted with ether and washed with 1N HCl and water. The ether solution was concentrated under reduced pressure and the crude product purified by flash chromatography over silica gel with dichloromethane/ether 99:1 to 95:5 to give 18.36 g of a mixture of 4-(2-methoxy-ethyl)-2-(6-trifluoromethyl-pyridin-3-yl)-pyrimidine-5-carboxylic acid methyl ester and 4-(2-methoxy-ethyl)-2-(6-trifluoromethyl-pyridin-3-yl)-pyrimidine-5-carboxylic acid ethyl ester.

MS: 342.2 and 356.3 (M+H)⁺.

c] [4-(2-Methoxy-ethyl)-2-(6-trifluoromethyl-pyridin-3-yl)-pyrimidin-5-yl]-methanol A 1.2 M solution of DIBALH in toluene (50 ml, 60 mmol) was dropped within 20 min to a dry ice cooled (−30° C.) solution of 4-(2-methoxy-ethyl)-2-(6-trifluoromethyl-pyridin-3-yl)-pyrimidine-5-carboxylic acid methyl ester and 4-(2-methoxy-ethyl)-2-(6-trifluoromethyl-pyridin-3-yl)-pyrimidine-5-carboxylic acid ethyl ester (6.83 g, 20 mmol) in THF (100 ml). The reaction mixture was warmed to 0° C., stirred for 1 h at this temperature, the cooling bath was removed and stirring was continued for 1 h at ambient temperature. The mixture was cooled to 0° C., neutralized with aqueous KHSO₄ solution (10%) and extracted three times with ether. The combined extracts were washed with aqueous NaCl solution (10%), dried (Na₂SO₄) and the solvent was removed under reduced pressure. The crude product was crystallized (dichloromethane/ether, 0° C.) to give 6.72 g (21.4 mmol, quant.) [4-(2-methoxy-ethyl)-2-(6-trifluoromethyl-pyridin-3-yl) -pyrimidin-5-yl]-methanol.
MS: 314.2 (M+H)$^+$.

d] {6-[4-(2-Methoxy-ethyl)-2-(6-trifluoromethyl-pyridin-3-yl)-pyrimidin-5-ylmethoxy]-indol-1-yl}-acetic acid ethyl ester In analogy to the procedure described in example 5 f], (6-hydroxy-indol-1-yl)-acetic acid ethyl ester (example 6 b]) was reacted with [4-(2-methoxy-ethyl)-2-(6-trifluoromethyl-pyridin-3-yl)-pyrimidin-5-yl]-methanol in the presence of tributylphosphine and N,N,N',N'-tetramethyl azodicarboxamide to yield the title compound as yellow solid.
MS: 515.3 (M+H)$^+$.

e] {6-[4-(2-Methoxy-ethyl)-2-(6-trifluoromethyl-pyridin-3-yl)-pyrimidin-5-ylmethoxy]-indol-1-yl}-acetic acid In analogy to the procedure described in example 5 g], {6-[4-(2-methoxy-ethyl)-2-(6-trifluoromethyl-pyridin-3-yl)-pyrimidin-5-ylmethoxy]-indol-1-yl}-acetic acid ethyl ester was treated with LiOH to obtain the title compound as yellow solid.
MS: 485.3 (M–H)$^-$.

Example 13

{6-[4-Trifluoromethyl-6-(4-trifluoromethyl-phenyl)-pyridin-3-ylmethoxy]-indol-1-yl}-acetic acid a] 4-Trifluoromethyl-6-(4-trifluoromethyl-phenyl)-nicotinic acid methyl ester [Following a procedure of K. Inada and N. Miyaura, Tetrahedron (2000), 56, 8661–8664]

To a solution of bis(triphenylphosphine)palladium(II) chloride (0.84 g, 1.2 mmol), methyl 6-chloro-4-(trifluoromethyl)nicotinate (9.58 g, 40 mmol) and 4-(trifluoromethyl) benzene boronic acid (10.1 g, 52 mmol) in degassed toluene (200 ml) was added aqueous 2 M K$_3$PO$_4$ (40 ml). The suspension was stirred at 80° C. for 16 h. The reaction mixture was cooled to RT, ice water was added and the mixture was extracted three times with diethyl ether. The organic phases were washed with aqueous 10% NaCl, dried (Na$_2$SO$_4$) and evaporated. Purification by flash-chromatography on silica gel (dichloromethane/heptane 2:1 to 1:1) gave 9.91 g (28.3 mmol, 71%) of the title compound as off-white powder.
MS: 348.9 (M)$^+$.

b] [4-Trifluoromethyl-6-(4-trifluoromethyl-phenyl)-pyridin-3-yl]-methanol

A 1.2 M solution of DIBALH in toluene (25 ml, 30 mmol) was dropped within 15 min to a dry ice cooled (–30° C.) solution of 5-(4-trifluoromethyl-phenyl)-pyrazine-2-carboxylic acid methyl ester (3.49 g, 10 mmol) in THF (50 ml). The reaction mixture was stirred for 1.3 h at –30° C. and for 1 h at 0° C. The mixture was neutralized with aqueous 10% KHSO$_4$ solution and extracted three times with ether. The combined organic layers were washed with 10% aqueous NaCl solution and dried over sodium sulfate. The solvent was removed under reduced pressure to give 3.21 g (10 mmol, quant.) of pure [4-trifluoromethyl-6-(4-trifluoromethyl-phenyl)-pyridin-3-yl]-methanol as light yellow powder.
MS: 321.0 (M)$^+$.

c] 5-Chloromethyl-4-trifluoromethyl-2-(4-trifluoromethyl-phenyl)-pyridine

In analogy to the procedure described in example 1 g], [4-trifluoromethyl-6-(4-trifluoromethyl-phenyl)-pyridin-3-yl]-methanol was reacted with thionyl chloride to give the title compound as off-white crystals.
MS: 339.0 (M, 1Cl)$^+$.

d] {6-[4-Trifluoromethyl-6-(4-trifluoromethyl-phenyl)-pyridin-3-ylmethoxy]-indol-1-yl}-acetic acid ethyl ester In analogy to the procedure described in example 7 a], (6-hydroxy-indol-1-yl)-acetic acid ethyl ester (example 6 b]) was reacted with 5-chloromethyl-4-trifluoromethyl-2-(4-trifluoromethyl-phenyl)-pyridine in the presence of cesium carbonate and potassium iodide, using acetonitrile as solvent, to obtain the title compound as white solid.

e] {6-[4-Trifluoromethyl-6-(4-trifluoromethyl-phenyl)-pyridin-3-ylmethoxy]1-indol-1-yl}-acetic acid In analogy to the procedure described in example 5 g], {6-[4-trifluoromethyl-6-(4-trifluoromethyl-phenyl)-pyridin-3-ylmethoxy]-indol-1-yl}-acetic acid ethyl ester was treated with LiOH to obtain the title compound as off-white solid.
MS: 495.3 (M–H)$^-$.

Example 14

{6-[4-(2-Methoxy-ethyl)-6-methyl-2-(4-trifluoromethyl-phenyl)-pyrimidin-5-ylmethoxy]-indol-1-yl}-acetic acid a] 2-Acetyl-5-methoxy-3-oxo-pentanoic acid methyl ester Pyridine (5.3 ml, 65.92 mmol) was dropped within 3 min to an ice cooled solution of 5-methoxy-3-oxo-pentanoic acid methyl ester (5.28 g, 32.96 mmol) and anhydrous magnesium chloride (3.14 g, 32.96 mmol) in dichloromethane (50 ml). Acetic anhydride (3.27 ml, 34.6 mmol) was added within 3 min. The reaction mixture was stirred over night at RT and after partial removal of the solvent under reduced pressure it was partitioned between ether and 1 N HCl/water. The ether solution was concentrated under reduced pressure to give 5.87 g (29 mmol, 88%) 2-acetyl-5-methoxy-3-oxo-pentanoic acid methyl ester.
MS: 203.3 (M+H)$^+$.

b] 5-Methoxy-2-[1-methoxy-eth-(E,Z)-ylidene]-3-oxo-pentanoic acid methyl ester

An ice-cooled solution of 2-acetyl-5-methoxy-3-oxo-pentanoic acid methyl ester (5.87 g, 29.02 mmol) in acetonitrile (50 ml) was treated with cesium carbonate (9.46 g, 29 mmol). After removal of the ice bath trifluoro-methanesulfonic acid methyl ester (3.28 ml, 29 mmol) was added. The reaction mixture was stirred for 2 h at RT, concentrated under reduced pressure, diluted with ether and washed with water. The ether-layers were concentrated under reduced pressure to provide 6 g (27.7 mmol, 96%) of crude 5-methoxy-2-[1-methoxy-eth-(E,Z)-ylidene]-3-oxo-pentanoic acid methyl ester.
MS: 217.3 (M+H)$^+$.

c] 4-(2-Methoxy-ethyl)-6-methyl-2-(4-trifluoromethyl-phenyl)-pyrimidine-5-carboxylic acid methyl ester A solution of 4-trifluoromethyl-benzamidine HCl (7.23 g, 27.5 mmol) in ethanol (30 ml) was treated with sodium tert-butoxide (2.67 g, 27.5 mmol). After 4 min a solution of 5-methoxy-2-[1-methoxy-eth-(E,Z)-ylidene]-3-oxo-pentanoic acid methyl ester (6 g, 27.7 mmol) in ethanol (30 ml) was added. The reaction mixture was stirred over night at ambient temperature, taken up in ether and washed with 1 N HCl and water. The crude product was purified by chromatography over silica gel with AcOEt/heptane 1:3, providing 4.9 g (13.8 mmol, 50%) of pure 4-(2-methoxy-ethyl)-6-methyl-2-(4-trifluoromethyl-phenyl)-pyrimidine-5-carboxylic acid methyl ester.

MS: 355.4 (M+H)$^+$.

d] [4-(2-Methoxy-ethyl)-6-methyl-2-(4-trifluoromethyl-phenyl)-pyrimidin-5-yl]-methanol A 1.2 M solution of DIBALH in toluene (34.6 ml, 41.5 mmol) was added dropwise to a dry-ice cooled solution of 4-(2-methoxy-ethyl)-6-methyl-2-(4-trifluoromethyl-phenyl)-pyrimidine-5-carboxylic acid methyl ester (4.9 g, 13.8 mmol) in tetrahydrofuran (50 ml). The reaction mixture was stirred for 15 min at −70° C., the dry-ice bath was removed and the reaction temperature was allowed to come to RT. The reaction mixture was stirred for 2 h at RT. Under ice-cooling 6 N aqueous HCl (10 ml) was carefully added. After 4 min ether was added, the layers were separated and the organic layer was washed with water, dried over sodium sulfate and concentrated under reduced pressure to give 4.67 g (14.3 mmol, quant.) of crystalline [4-(2-methoxy-ethyl)-6-methyl-2-(4-trifluoromethyl-phenyl)-pyrimidin-5-yl]-methanol.

MS: 327.1 (M+H)$^+$.

e] 5-Chloromethyl-4-(2-methoxy-ethyl)-6-methyl-2-(4-trifluoromethyl-phenyl)-pyrimidine A solution of [4-(2-methoxy-ethyl)-6-methyl-2-(4-trifluoromethyl-phenyl)-pyrimidin-5-yl]-methanol (2.47 g, 7.48 mmol) in dichloromethane (25 ml) was treated with thionylchloride (0.57 ml, 7.85 mmol). After 2 h stirring at RT, the mixture was partitioned between ether and water. The ether-phase was concentrated under reduced pressure to give 2.42 g (7 mmol, 94%) 5-chloromethyl-4-(2-methoxy-ethyl)-6-methyl-2-(4-trifluoromethyl-phenyl)-pyrimidine.

MS: 345.3 (M+H)$^+$.

f] {6-[4-(2-Methoxy-ethyl)-6-methyl-2-(4-trifluoromethyl-phenyl)-pyrimidin-5-ylmethoxy]-indol-1-yl}-acetic acid ethyl ester In analogy to the procedure described in example 7 a], (6-hydroxy-indol-1-yl)-acetic acid ethyl ester (example 6 b]) was reacted with 5-chloromethyl-4-(2-methoxy-ethyl)-6-methyl-2-(4-trifluoromethyl-phenyl)-pyrimidine in the presence of cesium carbonate and potassium iodide, using acetonitrile as solvent, to obtain the title compound as colorless crystals.

MS: 528.3 (M+H)$^+$.

g] {6-[4-(2-Methoxy-ethyl)-6-methyl-2-(4-trifluoromethyl-phenyl)-pyrimidin-5-ylmethoxy]-indol-1-yl}-acetic acid In analogy to the procedure described in example 5g], {6-[4-(2-methoxy-ethyl)-6-methyl-2-(4-trifluoromethyl-phenyl)-pyrimidin-5-ylmethoxy]-indol-1-yl}-acetic acid ethyl ester was treated with LiOH to obtain the title compound as colorless solid.

MS: 498.0 (M−H)$^-$.

Example 15

{6-[2-Methyl-4-trifluoromethyl-6-(4-trifluoromethyl-phenyl)-pyridin-3-ylmethoxy]-indol-1-yl}-acetic acid a] 2-Methyl-4-trifluoromethyl-6-(4-trifluoromethyl-phenyl)-nicotinic acid ethyl ester To an acetonitrile (50 ml) solution of (Z)-4,4,4-trifluoro-3-hydroxy-1-(4-trifluoromethyl-phenyl)-but-2-en-1-one (4.7 g, 17 mmol; D. Barrett, P. D. Bentley, T. R. Perrior, *Synthetic Commun.* 1996, 26, 3401–3406) was added ethyl-3-aminocrotonate (4.27 g, 33 mmol) under an argon atmosphere. The mixture was heated at reflux for 12 h. The solvent was removed under reduced pressure and the residue purified by column chromatography (silica gel, n-heptane/ethyl acetate) to yield 2.2 g (5.8 mmol, 35%) of the title compound as yellow crystals.

MS: 378.3 (M+H)$^+$.

b] [2-Methyl-4-trifluoromethyl-6-(4-trifluoromethyl-phenyl)-pyridin-3-yl]-methanol A solution of 2-methyl-4-trifluoromethyl-6-(4-trifluoromethyl-phenyl)-nicotinic acid ethyl ester (200 mg, 0.5 mmol) in diethyl ether (3 ml) was added to a suspension of lithium aluminium hydride (40 mg, 1 mmol) in diethyl ether (6 ml) under an argon atmosphere at ambient temperature within 5 min. The mixture was stirred at reflux for 12 h, cooled to 0° min. and treated cautiously with ice water (6 ml) and 10% aqueous NaOH (3 ml). The reaction mixture was filtered over celite, t-butyl methylether was added and the layers were separated. The aqueous layer was extracted one more time with t-butyl methylether, the combined organic layers were washed with ice water/brine 1/1 and dried over sodium sulfate. Removal of the solvent under reduced pressure gave a brown oil which was purified by column chromatography (silica gel, heptane/AcOEt) to yield 80 mg (240 μmol, 45%) of the title compound as yellow crystals.

MS: 336.2 (M+H)$^+$.

c] {6-[2-Methyl-4-trifluoromethyl-6-(4-trifluoromethyl-phenyl)-pyridin-3-ylmethoxy]-indol-1-yl}-acetic acid ethyl ester In analogy to the procedure described in example 5 f], (6-hydroxy-indol-1-yl)-acetic acid ethyl ester (example 6 b]) was reacted with [2-methyl-4-trifluoromethyl-6-(4-trifluoromethyl-phenyl)-pyridin-3-yl]-methanol in the presence of tributylphosphine and N,N,N',N'-tetramethyl azodicarboxamide to yield the title compound as colorless solid.

MS: 537.3 (M+H)$^+$.

d] {6-[2-Methyl-4-trifluoromethyl-6-(4-trifluoromethyl-phenyl)-pyridin-3-ylmethoxy]-indol-1-yl}-acetic acid In analogy to the procedure described in example 5 g], {6-[2-methyl-4-trifluoromethyl-6-(4-trifluoromethyl-phenyl)-pyridin-3-ylmethoxy]-indol-1-yl}-acetic acid ethyl ester was treated with LiOH to obtain the title compound as colorless solid.

MS: 507.2 (M−H)$^-$.

Example 16

{6-[2-Methyl-6-(4-trifluoromethoxy-phenyl)-4-trifluoromethyl-pyridin-3-ylmethoxy]-indol-1-yl}-acetic acid a] (Z) -4,4,4-Trifluoro-3-hydroxy-1-(4-trifluoromethoxy-phenyl)-but-2-en-1-one To a toluene (50 ml) suspension of potassium t-butoxide (3.3 g, 29 mmol) and 1-(4-trifluoromethoxy-phenyl)-ethanone (3.9 ml, 24 mmol) under an argon atmosphere was added dropwise ethyl trifluoroacetate (3.4 ml, 29 mmol) at 10° C. The suspension was stirred at ambient temperature for 14 h. The pH value of the mixture was adjusted to 6 with 10% $H_2SO_4$, the solution was extracted two times with t-butyl methylether and the combined extracts were washed with brine/ice water 1/1. The organic layer was dried over sodium sulfate, concentrated under reduced pressure and the residue purified by column chromatography (silica gel, n-heptane/ethyl acetate) to yield 2.9 g (9.7 mmol, 40%) of the title compound as orange oil.

MS: 319.2 (M+NH$_4$)$^+$.

b] 2-Methyl-6-(4-trifluoromethoxy-phenyl)-4-trifluoromethyl-nicotinic acid ethyl ester To an acetonitrile (35 ml) solution of (Z)-4,4,4-trifluoro-3-hydroxy-1-(4-trifluoromethoxy-phenyl)-but-2-en-1-one (2.9 g, 10 mmol) was added ethyl-3-aminocrotonate (2.5 g, 19 mmol) under an argon atmosphere. The mixture was heated at reflux for 12 h. The solvent was removed under reduced pressure and the residue purified by column chromatography (silica gel, n-heptane/ethyl acetate) to yield 1.9 g (4.8 mmol, 50%) of the title compound as yellow oil.

MS: 394.0 (M+H)$^+$.

c] [2-Methyl-6-(4-trifluoromethoxy-phenyl)-4-trifluoromethyl-pyridin-3-yl]-methanol A solution of 2-methyl-6-(4-trifluoromethoxy-phenyl)-4-trifluoromethyl-nicotinic acid ethyl ester (400 mg, 1 mmol) in diethyl ether (6 ml) was added to a suspension of lithium aluminium hydride (77 mg, 2 mmol) in diethyl ether (12 ml) under an argon atmosphere at ambient temperature within 5 min. The mixture was stirred at reflux for 12 h, cooled to 0° C. and treated cautiously with ice water (12 ml) and 10% aqueous NaOH (6 ml). The reaction mixture was filtered over celite, t-butyl methylether was added and the layers were separated. The aqueous layer was extracted one more time with t-butyl methylether, the combined organic layers were washed with ice water/brine 1/1 and dried over sodium sulfate. Removal of the solvent under reduced pressure gave an orange oil which was purified by column chromatography (silica gel, heptane/AcOEt) to yield 140 mg (400 μmol, 39%) of the title compound as colorless crystals.

MS: 352.3 (M+H)$^+$.

d] {6-[2-Methyl-6-(4-trifluoromethoxy-phenyl)-4-trifluoromethyl-pyridin-3-ylmethoxy]-indol-1-yl}-acetic acid ethyl ester In analogy to the procedure described in example 5 f], (6-hydroxy-indol-1-yl)-acetic acid ethyl ester (example 6 b]) was reacted with [2-methyl-6-(4-trifluoromethoxy-phenyl)-4-trifluoromethyl-pyridin-3-yl]-methanol in the presence of tributylphosphine and N,N,N',N'-tetramethyl azodicarboxamide to yield the title compound as colorless solid.

MS: 553.2 (M+H)$^+$.

e] {6-[2-Methyl-6-(4-trifluoromethoxy-phenyl)-4-trifluoromethyl-pyridin-3-ylmethoxy]-indol-1-yl}-acetic acid In analogy to the procedure described in example 5 g], {6-[2-methyl-6-(4-trifluoromethoxy-phenyl)-4-trifluoromethyl-pyridin-3-ylmethoxy]-indol-1-yl}-acetic acid ethyl ester was treated with LiOH to obtain the title compound as colorless solid.

MS: 525.0 (M+H)$^+$.

Example 17

{6-[6-(4-Trifluoromethoxy-phenyl)-4-trifluoromethyl-pyridin-3-ylmethoxy]-indol-1-yl}-acetic acid a] 6-(4-Trifluoromethoxy-phenyl)-4-trifluoromethyl-nicotinic acid methyl ester In analogy to the procedure described in example 13 a], 4-(trifluoromethoxy)-phenylboronic acid was reacted with methyl 6-chloro-4-(trifluoromethyl)nicotinate in the presence of bis(triphenylphosphine)palladium(II)chloride and aqueous 2M K$_3$PO$_4$ solution to give the title compound as yellow crystals.

MS: 366.0 (M+H)$^+$.

b] [6-(4-Trifluoromethoxy-phenyl)-4-trifluoromethyl-pyridin-3-yl]-methanol

In analogy to the procedure described in example 16 c], 6-(4-trifluoromethoxy-phenyl)-4-trifluoromethyl-nicotinic acid methyl ester was treated with lithium aluminium hydride in tetrahydrofuran under reflux conditions for 12 h to give the title compound as yellow oil.

MS: 338.0 (M+H)$^+$.

c] {6-[6-(4-Trifluoromethoxy-phenyl)-4-trifluoromethyl-pyridin-3-ylmethoxy]-indol-1-yl}-acetic acid ethyl ester In analogy to the procedure described in example 5 f], (6-hydroxy-indol-1-yl)-acetic acid ethyl ester (example 6 b]) was reacted with [6-(4-trifluoromethoxy-phenyl)-4-trifluoromethyl-pyridin-3-yl]-methanol in the presence of tributylphosphine and N,N,N',N'-tetramethyl azodicarboxamide to yield the title compound as colorless foam.

MS: 539.3 (M+H)$^+$.

d] {6-[6-(4-Trifluoromethoxy-phenyl)-4-trifluoromethyl-pyridin-3-ylmethoxy]-indol-1-yl}-acetic acid In analogy to the procedure described in example 5 g], {6-[6-(4-trifluoromethoxy-phenyl)-4-trifluoromethyl-pyridin-3-ylmethoxy]-indol-1-yl}-acetic acid ethyl ester was treated with LiOH to obtain the title compound as yellow solid.

MS: 511.4 (M+H)$^+$.

Example 18

{6-[2-Cyclopropylmethyl-6-(4-trifluoromethoxy-phenyl)-4-trifluoromethyl-pyridin-3-ylmethoxy]-indol-1-yl}-acetic acid a] 2-Cyclopropyl-acetimidic acid methyl ester hydrochloride Methanol (4.9 ml, 120 mmol) was added to a solution of cyclopropylacetonitrile (11.2 ml, 120 mmol) in diethyl ether (60 ml). The solution was cooled to 4° C. and HCl gas was bubbled through the solution for 3 h. The mixture was stirred for 14 h at ambient temperature and the solvent removed under reduced pressure. The residue was washed with pentane and diethyl ether to give 10.3 g (69 mmol, 58%) of the title compound as colorless crystals which were used in the next step without further purification.

b] 5-(1-Amino-2-cyclopropyl-ethylidene)-2,2-dimethyl-[1,3]dioxane-4,6-dione

2-Cyclopropyl-acetimidic acid methyl ester hydrochloride (1 g, 7 mmol), 2,2-dimethyl-[1,3]dioxane-4,6-dione (963 mg, 7 mmol) and triethylamine (1.07 ml, 8 mmol) in chloroform (7 ml) were heated under reflux conditions for 14 h. The mixture was diluted with dichloromethane, washed neutral with brine/ice water 1/1 and the organic layer was dried over sodium sulfate. The solvent was removed under reduced pressure and the residue purified by flash chromatography (silica gel, heptane/AcOEt) to give 128 mg (0.6 mmol, 9%) of the title compound as yellow crystals.

c] 3-Amino-4-cyclopropyl-but-2-enoic acid ethyl ester 5-(1-Amino-2-cyclopropyl-ethylidene)-2,2-dimethyl-[1,3]dioxane-4,6-dione (397 mg, 2 mmol) was added to a solution of sodium (45 mg, 2 mmol) in ethanol (3 ml). The reaction mixture was heated under reflux for 14 h, diluted with dichloromethane and poured onto ice water/brine 1/1. The organic layer was dried over sodium sulfate and the solvent removed under reduced pressure to give 231 mg (1.4 mmol, 77%) of the title compound as orange oil.
MS: 170.3 (M+H)$^+$.

d] 2-Cyclopropylmethyl-6-(4-trifluoromethoxy-phenyl)-4-trifluoromethyl-nicotinic acid ethyl ester 3-Amino-4-cyclopropyl-but-2-enoic acid ethyl ester (231 mg, 1.4 mmol) was added to a solution of (Z)-4,4,4-trifluoro-3-hydroxy-1-(4-trifluoromethoxy-phenyl)-but-2-en-1-one (819 mg, 2.7 mmol; example 16 a]) in acetonitrile (2.7 ml). The mixture was heated under reflux conditions for 12 h, the solvent was removed under reduced pressure and the residue purified by flash chromatography (silica gel, heptane/AcOEt) to give 242 mg (0.56 mmol, 41%) of the title compound as yellow oil.
MS: 434.3 (M+H)$^+$.

e] [2-Cyclopropylmethyl-6-(4-trifluoromethoxy-phenyl)-4-trifluoromethyl-pyridin-3-yl]-methanol In analogy to the procedure described in example 16 c], 2-cyclopropylmethyl-6-(4-trifluoromethoxy-phenyl)-4-trifluoromethyl-nicotinic acid ethyl ester was treated with lithium aluminium hydride to give the title compound as colorless crystals.
MS: 392.3 (M+H)$^+$.

f] {6-[2-Cyclopropylmethyl-6-(4-trifluoromethoxy-phenyl)-4-trifluoromethyl-pyridin-3-ylmethoxy]-indol-1-yl}-acetic acid ethyl ester In analogy to the procedure described in example 5 f], (6-hydroxy-indol-1-yl)-acetic acid ethyl ester (example 6 b]) was reacted with [2-cyclopropylmethyl-6-(4-trifluoromethoxy-phenyl)-4-trifluoromethyl-pyridin-3-yl]-methanol in the presence of tributylphosphine and N,N,N',N'-tetramethyl azodicarboxamide to yield the title compound as colorless solid.
MS: 593.3 (M+H)$^+$.

g] {6-[2-Cyclopropylmethyl-6-(4-trifluoromethoxy-phenyl)-4-trifluoromethyl-pyridin-3-ylmethoxy]-indol-1-yl}-acetic acid In analogy to the procedure described in example 5 g], {6-[2-cyclopropylmethyl-6-(4-trifluoromethoxy-phenyl)-4-trifluoromethyl-pyridin-3-ylmethoxy]-indol-1-yl}-acetic acid ethyl ester was treated with LiOH to obtain the title compound as brown solid.
MS: 565.5 (M+H)$^+$.

Example 19

(6-{2-[4-Cyclopropyl-2-(4-trifluoromethyl-phenyl)-pyrimidin-5-yl]-ethoxy}-indol-1-yl)-acetic acid a] [4-Cyclopropyl-2-(4-trifluoromethyl-phenyl)-pyrimidin-5-yl]-acetonitrile In analogy to the procedure described in example 8 b], 5-chloromethyl-4-cyclopropyl-2-(4-trifluoromethyl-phenyl)-pyrimidine (example 3 d]) was reacted with sodium cyanide to give the title compound as white crystals.
MS: 304.2 (M+H)$^+$.

b] [4-Cyclopropyl-2-(4-trifluoromethyl-phenyl)-pyrimidin-5-yl]-acetic acid

In analogy to the procedure described in example 8 c], [4-cyclopropyl-2-(4-trifluoromethyl-phenyl)-pyrimidin-5-yl]-acetonitrile was treated with sodium hydroxide to give the title compound as white crystals.
MS: 643.2 (2M−H)$^−$.

c] [4-Cyclopropyl-2-(4-trifluoromethyl-phenyl)-pyrimidin-5-yl]-acetic acid methyl ester In analogy to the procedure described in example 8 d], [4-cyclopropyl-2-(4-trifluoromethyl-phenyl)-pyrimidin-5-yl]-acetic acid was esterified with methanol to give the title compound as yellow solid.
MS: 336.0 (M)$^+$.

d] 2-[4-Cyclopropyl-2-(4-trifluoromethyl-phenyl)-pyrimidin-5-yl]-ethanol

In analogy to the procedure described in example 1 f], [4-cyclopropyl-2-(4-trifluoromethyl-phenyl)-pyrimidin-5-yl]-acetic acid methyl ester was reacted with DIBAL-H to give the title compound as yellow solid.
MS: 309.1 (M+H)$^+$.

e] (6-{2-[4-Cyclopropyl-2-(4-trifluoromethyl-phenyl)-pyrimidin-5-yl]-ethoxy}-indol-1-yl)-acetic acid ethyl ester In analogy to the procedure described in example 5 f], (6-hydroxy-indol-1-yl)-acetic acid ethyl ester (example 6 b]) was reacted with 2-[4-cyclopropyl-2-(4-trifluoromethyl-phenyl)-pyrimidin-5-yl]-ethanol in the presence of di-tert-butyl azodicarboxylate and triphenylphosphine in tetrahydrofuran to yield the title compound as colorless liquid.
MS: 510.5 (M+H)$^+$.

f] (6-{2-[4-Cyclopropyl-2-(4-trifluoromethyl-phenyl)-pyrimidin-5-yl]-ethoxy}-indol-1-yl)-acetic acid In analogy to the procedure described in example 5 g], (6-{2-[4-cyclopropyl-2-(4-trifluoromethyl-phenyl)-pyrimidin-5-yl]-ethoxy}-indol-1-yl)-acetic acid ethyl ester was treated with LiOH to obtain the title compound as yellow solid.
MS: 482.5 (M+H)$^+$.

Example 20

{6-[6-(4-Trifluoromethoxy-phenyl)-2-trifluoromethyl-pyridin-3-ylmethoxy]-indol-1-yl}-acetic acid a] (E)-3-Dimethylamino-1-(4-trifluoromethoxy-phenyl)-propenone (Following the procedure described in Gammill, R. B., Synthesis (1979), (11), 901–903)

A solution of 1-(4-trifluoromethoxy-phenyl)-ethanone (20.4 g, 100 mmol) in dimethylformamide dimethylacetal (20 ml, 150 mmol) was heated to 100° C. for 24 h. The solvent was removed under reduced pressure and the crude product crystallized from ether/n-pentane to give 23.1 g (89 mmol, 89%) of the title compound as yellow solid.
MS: 260.1 (M+H)$^+$.

b] 6-(4-Trifluoromethoxy-phenyl)-2-trifluoromethyl-nicotinic acid ethyl ester (Following the procedure described in Al-Saleh, B.; Abdelkhalik, M. M.; Eltoukhy, A. M.; Elnagdi, M. H., Journal of Heterocyclic Chemistry (2002), 39(5), 1035–1038)

A mixture of (E)-3-dimethylamino-1-(4-trifluoromethoxy-phenyl)-propenone(1 g, 3.9 mmol), 4,4,4-trifluoro-3-oxobutanoic acid ethyl ester (880 mg, 4.6 mmol) and ammonium acetate (387 mg, 5 mmol) in acetic acid (3.9 ml) was heated under reflux conditions for 1 h. The solvent was removed under reduced pressure and the residue was partitioned between aqueous saturated NaHCO$_3$/ice water and ethyl acetate. The aqueous layer was extracted two times with ethyl acetate, the combined extracts were washed with brine and dried over sodium sulfate. The solvent was removed under reduced pressure and the residue purified by flash chromatography (SiO$_2$, n-heptane/AcOEt) to give 68 mg (0.18 mmol, 5%) of the title compound as yellow oil.
MS: 338.0 (M+H)$^+$.

c] [6-(4-Trifluoromethoxy-phenyl)-2-trifluoromethyl-pyridin-3-yl]-methanol

In analogy to the procedure described in example 16 c], 6-(4-trifluoromethoxy-phenyl)-2-trifluoromethyl-nicotinic acid ethyl ester was treated with lithium aluminium hydride to give the title compound as colorless crystals.
MS: 338.0 (M+H)$^+$.

d] {6-[6-(4-Trifluoromethoxy-phenyl)-2-trifluoromethyl-pyridin-3-ylmethoxy]-indol-1-yl}-acetic acid ethyl ester In analogy to the procedure described in example 5 f], (6-hydroxy-indol-1-yl)-acetic acid ethyl ester (example 6 b]) was reacted with [6-(4-trifluoromethoxy-phenyl)-2-trifluoromethyl-pyridin-3-yl]-methanol in the presence of tributylphosphine and N,N,N',N'-tetramethyl azodicarboxamide in tetrahydrofuran to yield the title compound as colorless crystals.
MS: 539.3 (M+H)$^+$.

e] {6-[6-(4-Trifluoromethoxy-phenyl)-2-trifluoromethyl-pyridin-3-ylmethoxy]-indol-1-yl}-acetic acid In analogy to the procedure described in example 5 g], {6-[6-(4-trifluoromethoxy-phenyl)-2-trifluoromethyl-pyridin-3-ylmethoxy]-indol-1-yl}-acetic acid ethyl ester was treated with LiOH to obtain the title compound as colorless solid.
MS: 511.4 (M+H)$^+$.

Example 21

{6-[2-Cyclopropyl-6-(4-trifluoromethoxy-phenyl)-4-trifluoromethyl-pyridin-3-ylmethoxy]-indol-1-yl}-acetic acid a] 2-Cyclopropyl-6-(4-trifluoromethoxy-phenyl)-4-trifluoromethyl-nicotinic acid ethyl ester In analogy to the procedure described in example 18 d], 3-amino-3-cyclopropyl-acrylic acid ethyl ester (J. P. Célérier, E. Deloisy, P. Kapron, G. Lhommet, P. Maitte, Synthesis 1981, 130–133) was reacted with (Z)-4,4,4-trifluoro-3-hydroxy-1-(4-trifluoromethoxy-phenyl)-but-2-en-1-one (example 16 a]) to give the title compound as colorless oil.
MS: 420.3 (M+H)$^+$.

b] [2-Cyclopropyl-6-(4-trifluoromethoxy-phenyl)-4-trifluoromethyl-pyridin-3-yl]-methanol In analogy to the procedure described in example 16 c], 2-cyclopropyl-6-(4-trifluoromethoxy-phenyl)-4-trifluoromethyl-nicotinic acid ethyl ester was treated with lithium aluminium hydride to give the title compound as colorless crystals.
MS: 378.3 (M+H)$^+$. cl {6-[2-Cyclopropyl-6-(4-trifluoromethoxy-phenyl)-4-trifluoromethyl-pyridin-3-ylmethoxy]-indol-1-yl}-acetic acid ethyl ester In analogy to the procedure described in example 5 f], (6-hydroxy-indol-1-yl)-acetic acid ethyl ester (example 6 b]) was reacted with [2-cyclopropyl-6-(4-trifluoromethoxy-phenyl)-4-trifluoromethyl-pyridin-3-yl]-methanol in the presence of tributylphosphine and N,N,N',N'-tetramethyl azodicarboxamide in tetrahydrofuran to yield the title compound as colorless solid.
MS: 579.3 (M+H)$^+$.

d] {6-[2-Cyclopropyl-6-(4-trifluoromethoxy-phenyl)-4-trifluoromethyl-pyridin-3-ylmethoxy]-indol-1-yl}-acetic acid In analogy to the procedure described in example 5 g], {6-[2-cyclopropyl-6-(4-trifluoromethoxy-phenyl)-4-trifluoromethyl-pyridin-3-ylmethoxy]-indol-1-yl}-acetic acid ethyl ester was treated with LiOH to obtain the title compound as pink solid.
MS: 551.0 (M+H)$^+$.

Example A

Film coated tablets containing the following ingredients can be manufactured in a convential manner.

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcristalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |

-continued

| | |
|---|---|
| Sodium carbonate | to obtain a final pH of 7 |
| Water for injection solutions | ad 1.0 ml |

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavoring additives and filled into sachets.

What is claimed:
1. A Compound of the formula

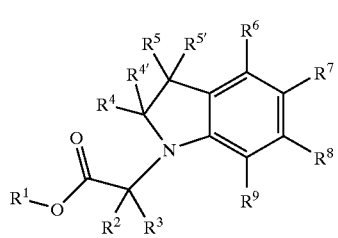

I wherein
$R^1$ is hydrogen or $C_{1-7}$-alkyl;
$R^2$ and $R^3$ independently from each other are hydrogen or $C_{1-7}$-alkyl;
$R^4$ and $R^5$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl or fluoro-$C_{1-7}$-alkyl;
$R^{4'}$ and $R^{5'}$ together form a double bond, or $R^{4'}$ and $R^{5'}$ are hydrogen;
$R^6$, $R^7$, $R^8$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
and one of $R^6$, $R^7$ and $R^8$ is

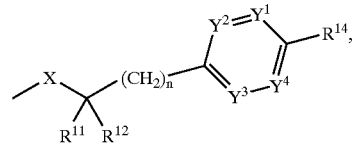

wherein
X is S, O, $NR^{10}$,
$R^{10}$ is hydrogen, $C_{1-7}$-alkyl, $C_{3-7}$-cycloalkyl, fluoro-$C_{1-7}$-alkyl;
$R^{11}$ and $R^{12}$ are independently from each other hydrogen, $C_{1-7}$-alkyl, $C_{3-7}$-cycloalkyl, fluoro-$C_{1-7}$-alkyl or fluoro;
$Y^1$, $Y^2$, $Y^3$ and $Y^4$ are N or C—$R^{13}$ and 1 or 2 of $Y^1$, $Y^2$, $Y^3$ and $Y^4$ are N and the other ones are C—$R^{13}$;
$R^{13}$ is selected from the group consisting of hydrogen, $C_{1-7}$-alkyl, $C_{3-7}$-cycloalkyl, $C_{3-7}$-cycloalkyl-$C_{1-7}$-alkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;
$R^{14}$ is aryl or heteroaryl;
n is 0, 1 or 2; and
pharmaceutically acceptable salts and/or esters thereof.
2. The Compound of claim 1, wherein
$R^1$ is hydrogen or $C_{1-7}$-alkyl;
$R^2$ and $R^3$ independently from each other are hydrogen or $C_{1-7}$-alkyl;
$R^4$ and $R^5$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl or fluoro-$C_{1-7}$-alkyl;
$R^{4'}$ and $R^{5'}$ together form a double bond, or $R^{4'}$ and $R^{5'}$ are hydrogen;
$R^6$, $R^7$, $R^8$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
and one of $R^6$, $R^7$ and $R^8$ is

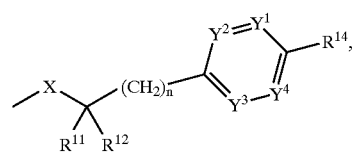

wherein
X is S, O, $NR^{10}$,
$R^{10}$ is hydrogen, $C_{1-7}$-alkyl, $C_{3-7}$-cycloalkyl, fluoro-$C_{1-7}$-alkyl;
$R^{11}$ and $R^{12}$ are independently from each other hydrogen, $C_{1-7}$-alkyl, $C_{3-7}$-cycloalkyl, fluoro-$C_{1-7}$-alkyl or fluoro;
$Y^1$, $Y^2$, $Y^3$ and $Y^4$ are N or C—$R^{13}$ and 1 or 2 of $Y^1$, $Y^2$, $Y^3$ and $Y^4$ are N and the other ones are C—$R^{13}$;
$R^{13}$ is selected from the group consisting of hydrogen, $C_{1-7}$-alkyl, $C_{3-7}$-cycloalkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;
$R^{14}$ is aryl or heteroaryl;
n is 0, 1 or 2; and
all enantiomers and pharmaceutically acceptable salts and/or esters thereof.

3. The Compound of claim 2 having the formula

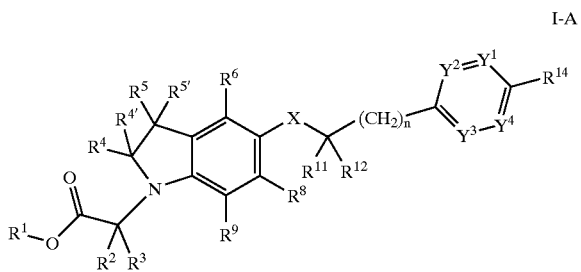

I-A wherein
X, $Y^1$ to $Y^4$, $R^1$, $R^2$, $R^3$, $R^4$, $R^{4'}$, $R^5$, $R^{5'}$, $R^{11}$, $R^{12}$, $R^{14}$ and n are as defined in claim 1;
$R^6$, $R^8$ and $R^9$ are selected from the group consisting of hydrogen; $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and
all enantiomers and pharmaceutically acceptable salts and/or esters thereof.

4. The Compound of claim 3, wherein $R^6$, $R^8$ and $R^9$ are hydrogen.

5. The Compound of claim 2 having the formula

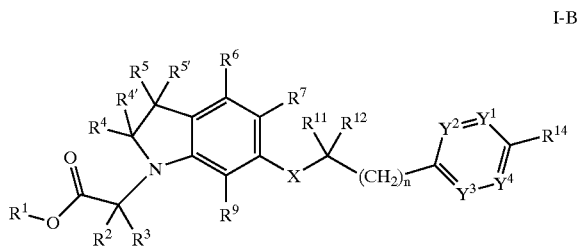

I-B wherein
X, $Y^1$ to $Y^4$, $R^1$, $R^2$, $R^3$, $R^4$, $R^{4'}$, $R^5$, $R^{5'}$, $R^{11}$, $R^{12}$, $R^{14}$ and n are as defined in claim 2;
$R^6$, $R^7$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and
all enantiomers and pharmaceutically acceptable salts and/or esters thereof.

6. The Compound of claim 5, wherein $R^6$, $R^7$ and $R^9$ are hydrogen.

7. The Compound of claim 2 having the formula

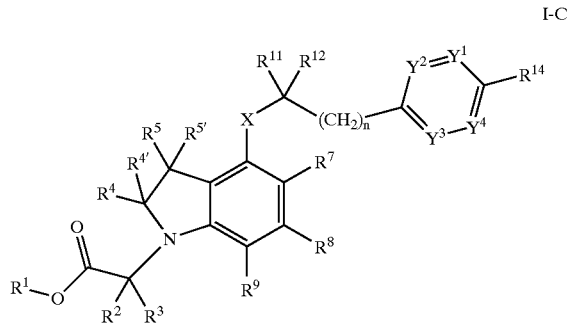

I-C wherein
X, $Y^1$ to $Y^4$, $R^1$, $R^2$, $R^3$, $R^4$, $R^{4'}$, $R^5$, $R^{5'}$, $R^{11}$, $R^{12}$, $R^{14}$ and n are as defined in claim 2;
$R^7$, $R^8$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano; and
all enantiomers and pharmaceutically acceptable salts and/or esters thereof.

8. The Compound of claim 7, wherein $R^7$, $R^8$ and $R^9$ are hydrogen.

9. The Compound of claim 8, wherein $R^1$ is hydrogen.

10. The Compound of claim 9, wherein $R^2$ and $R^3$ independently from each other are hydrogen or methyl.

11. The Compound of claim 10, wherein $R^{4'}$ and $R^{5'}$ together form a double bond.

12. The Compound of claim 11, wherein $R^4$ and $R^5$ are hydrogen.

13. The Compound of claim 12, wherein X is O.

14. The Compound of claim 12, wherein X is $NR^{10}$, and $R^{10}$ is hydrogen, $C_{1-7}$-alkyl, $C_{3-7}$-cycloalkyl or fluoro-$C_{1-7}$-alkyl.

15. The Compound of claim 14, wherein $R^{10}$ is $C_{1-7}$-alkyl.

16. The Compound of claim 12, wherein X is S.

17. The Compound of claim 16, wherein $R^{11}$ and $R^{12}$ are hydrogen.

18. The Compound of claim 17, wherein $R^{14}$ is unsubstituted phenyl or phenyl substituted with one to three groups selected from $C_{1-7}$-alkyl, $C_{1-7}$-alkoxy, halogen, fluoro-$C_{1-7}$-alkyl, fluoro-$C_{1-7}$-alkoxy and cyano.

19. The Compound of claim 18, wherein $R^{14}$ is phenyl substituted with halogen, fluoro-$C_{1-7}$-alkoxy, or fluoro-$C_{1-7}$-alkyl.

20. The Compound of claim 19, wherein $R^{14}$ is 4-trifluoro-methylphenyl.

21. The Compound of claim 20, wherein $Y^1$ is N and $Y^2$, $Y^3$ and $Y^4$ are C—$R^{13}$ or wherein $Y^1$ and $Y^4$ are N and $Y^2$ and $Y^3$ are C—$R^{13}$.

22. The Compound of claim 21, wherein at least one of $R^{13}$ is $C_{1-7}$-alkyl, $C_{3-7}$-cycloalkyl, fluoro-$C_{1-7}$-alkyl or $C_{1-7}$-alkoxy-$C_{1-7}$-alkyl.

23. The Compound of claim 1, wherein said compound is selected from the group consisting of
{5-[4-(2-methoxy-ethyl)-2-(4-trifluoromethyl-phenyl)-pyrimidin-5-ylmethoxy]-indol-1-yl}-acetic acid;
{5-[4-methyl-2-(4-trifluoromethyl-phenyl)-pyrimidin-5-ylmethoxy]-indol-1-yl}-acetic acid;

{5-[4-cyclopropyl-2-(4-trifluoromethyl-phenyl)-pyrimidin-5-ylmethoxy]-indol-1-yl}-acetic acid;

(5-{methyl-[4-methyl-2-(4-trifluoromethyl-phenyl)-pyrimidin-5-ylmethyl]-amino}-indol-1-yl)-acetic acid;

{6-[2-methyl-6-(4-trifluoromethyl-phenyl)-pyridin-3-ylmethoxy]-indol-1-yl}-acetic acid;

{6-[2-methyl-6-(4-trifluoromethyl-phenyl)-pyridin-3-ylmethoxy]-2,3-dihydro-indol-1-yl}-acetic acid;

{6-[4-cyclopropyl-2-(4-trifluoromethyl-phenyl)-pyrimidin-5-ylmethoxy]-indol-1-yl}-acetic acid;

(6-{2-[2-methyl-6-(4-trifluoromethyl-phenyl)-pyridin-3-yl]-ethoxy}-indol-1-yl)-acetic acid;

{6-[6-(4-trifluoromethoxy-phenyl)-pyridin-3-ylmethoxy]-indol-1-yl}-acetic acid;

{6-[2-methyl-6-(3-trifluoromethyl-phenyl)-pyridin-3-ylmethoxy]-indol-1-yl}-acetic acid;

(4-{2-[2-methyl-6-(4-trifluoromethyl-phenyl)-pyridin-3-yl]-ethoxy}-indol-1-yl)-acetic acid;

{6-[4-(2-methoxy-ethyl)-2-(6-trifluoromethyl-pyridin-3-yl)-pyrimidin-5-ylmethoxy]-indol-1-yl}-acetic acid;

{6-[4-trifluoromethyl-6-(4-trifluoromethyl-phenyl)-pyridin-3-ylmethoxy]-indol-1-yl}-acetic acid;

{6-[4-(2-methoxy-ethyl)-6-methyl-2-(4-trifluoromethyl-phenyl)-pyrimidin-5-ylmethoxy]-indol-1-yl}-acetic acid;

{6-[2-methyl-4-trifluoromethyl-6-(4-trifluoromethyl-phenyl)-pyridin-3-ylmethoxy]-indol-1-yl}-acetic acid;

{6-[2-methyl-6-(4-trifluoromethoxy-phenyl)-4-trifluoromethyl-pyridin-3-ylmethoxy]-indol-1-yl}-acetic acid;

{6-[6-(4-trifluoromethoxy-phenyl)-4-trifluoromethyl-pyridin-3-ylmethoxy]-indol-1-yl}-acetic acid;

{6-[2-cyclopropylmethyl-6-(4-trifluoromethoxy-phenyl)-4-trifluoromethyl-pyridin-3-ylmethoxy]-indol-1-yl}-acetic acid;

(6-{2-[4-cyclopropyl-2-(4-trifluoromethyl-phenyl)-pyrimidin-5-yl]-ethoxy}-indol-1-yl)-acetic acid;

{6-[6-(4-trifluoromethoxy-phenyl)-2-trifluoromethyl-pyridin-3-ylmethoxy]-indol-1-yl}-acetic acid; and {6-[2-cyclopropyl-6-(4-trifluoromethoxy-phenyl)-4-trifluoromethyl-pyridin-3-ylmethoxy]-indol-1-yl}-acetic acid.

24. A process for the manufacture of a compound of claim 1, which process comprises a) reacting a compound of formula

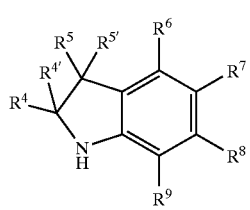

II wherein $R^4$ to $R^9$ are as defined in claim 1, with a compound of formula

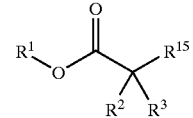

III wherein $R^1$ is $C_{1-7}$-alkyl, $R^2$ and $R^3$ are as defined in claim 1 and $R^{15}$ is halogen, triflate or another leaving group, to obtain a compound of formula

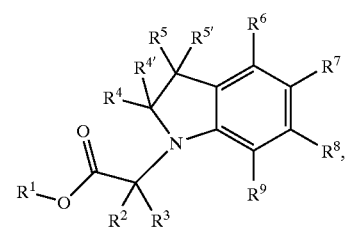

I wherein $R^1$ is $C_{1-7}$-alkyl and $R^2$ to $R^9$ are as defined in claim 1, and optionally hydrolysing the ester group to obtain a compound of formula I, wherein $R^1$ is hydrogen, or, alternatively, b) reacting a compound of formula

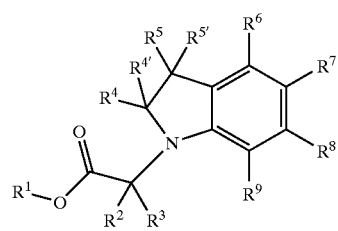

IV wherein $R^1$ is $C_{1-7}$-alkyl, $R^2$ to $R^{5'}$ are as defined in claim 1 and $R^6$, $R^7$, $R^8$ and $R^9$ are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl and cyano, and one of $R^6$, $R^7$ or $R^8$ is —OH, —SH or —NHR$^{10}$ with $R^{10}$ being hydrogen, $C_{1-7}$-alkyl, $C_{3-7}$-cycloalkyl or fluoro-$C_{1-7}$-alkyl, with a compound of formula

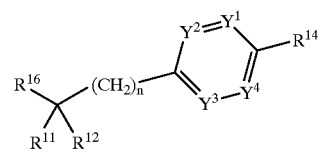

V wherein $Y^1, Y^2, Y^3, Y^4, R^{11}, R^{12}, R^{14}$ and n are as defined in claim 1 and $R^{16}$ is —OH, —Cl, —Br, —I or another leaving group, to obtain a compound of formula

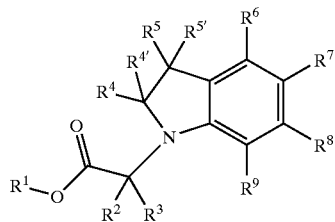

wherein $R^1$ is $C_{1-7}$-alkyl and $R^2$ to $R^9$ are as defined in claim 1,
and optionally hydrolysing the ester group to obtain a compound of formula I, wherein $R^1$ is hydrogen.

25. A pharmaceutical composition comprising a compound of the formula

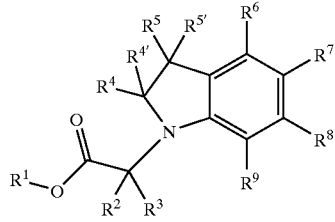

wherein
$R^1$ is hydrogen or $C_{1-7}$-alkyl;
$R^2$ and $R^3$ independently from each other are hydrogen or $C_{1-7}$-alkyl;
$R^4$ and $R^5$ are selected from the group consisting of independently from each other hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl or fluoro-$C_{1-7}$-alkyl;

$R^{4'}$ and $R^{5'}$ together form a double bond, or $R^{4'}$ and $R^{5'}$ are hydrogen;
$R^6$, $R^7$, $R^8$ and $R^9$ independently from each other are selected from the group consisting of hydrogen, $C_{1-7}$-alkyl, $C_{3-7}$-cycloalkyl, halogen, $C_{1-7}$-alkoxy-$C_{1-7}$-alkyl, $C_{2-7}$-alkenyl, $C_{2-7}$-alkinyl, fluoro-$C_{1-7}$-alkyl, cyano-$C_{1-7}$-alkyl or cyano;
and one of $R^6$, $R^7$ and $R^8$ is

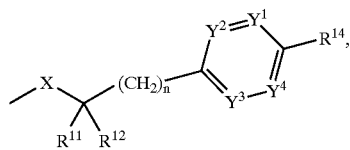

wherein
X is S, O, $NR^{10}$,
$R^{10}$ is hydrogen, $C_{1-7}$-alkyl, $C_{3-7}$-cycloalkyl, fluoro-$C_{1-7}$-alkyl;
$R^{11}$ and $R^{12}$ are independently from each other hydrogen, $C_{1-7}$-alkyl, $C_{3-7}$-cycloalkyl, fluoro-$C_{1-7}$-alkyl or fluoro;
$Y^1$, $Y^2$, $Y^3$ and $Y^4$ are N or C—$R^{13}$ and 1 or 2 of $Y^1$, $Y^2$, $Y^3$ and $Y^4$ are N and the other ones are C—$R^{13}$;
$R^{13}$ independently from each other in each occurance is selected from the group consisting of hydrogen, $C_{1-7}$-alkyl, $C_{3-7}$-cycloalkyl, $C_{3-7}$-cycloalkyl-$C_{1-7}$-alkyl, fluoro-$C_{1-7}$-alkyl, $C_{1-7}$-alkoxy-$C_{1-7}$-alkyl, hydroxy-$C_{1-7}$-alkyl, $C_{1-7}$-alkylthio-$C_{1-7}$-alkyl, carboxy-$C_{1-7}$-alkoxy-$C_{1-7}$-alkyl, carboxy, carboxy-$C_{1-7}$-alkyl, mono- or di-$C_{1-7}$-alkyl-amino-$C_{1-7}$-alkyl, $C_{1-7}$-alkanoyl-$C_{1-7}$-alkyl, $C_{2-7}$-alkenyl, and $C_{2-7}$-alkinyl;
$R^{14}$ is aryl or heteroaryl;
n is 0, 1 or 2; and
pharmaceutically acceptable salts and/or esters thereof and a pharmaceutically acceptable carrier and/or adjuvant.

\* \* \* \* \*

UNITED STATES PATENT AND TRADEMARK OFFICE
CERTIFICATE OF CORRECTION

PATENT NO. : 6,995,263 B2
DATED : February 7, 2006
INVENTOR(S) : Jean Ackermann et al.

It is certified that error appears in the above-identified patent and that said Letters Patent is hereby corrected as shown below:

Title page,
Item [75], Inventors, "Jean Ackermann, Richen (CH); Johannes Aebi, Basel (CH); Alfred Binggeli, Basel (CH);..." should be -- Jean Ackermann, Richen (CH); Johannes Aebi, Basel (CH); Alfred Binggeli, Binningen (CH);... --.

Signed and Sealed this

Sixth Day of June, 2006

JON W. DUDAS
*Director of the United States Patent and Trademark Office*